United States Patent
Tanaka et al.

(10) Patent No.: US 11,468,589 B2
(45) Date of Patent: Oct. 11, 2022

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Toru Tanaka, Funabashi (JP); Kiyohide Satoh, Kawasaki (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 489 days.

(21) Appl. No.: 16/288,931

(22) Filed: Feb. 28, 2019

(65) Prior Publication Data
US 2019/0197723 A1 Jun. 27, 2019

Related U.S. Application Data

(63) Continuation of application No. PCT/JP2017/031194, filed on Aug. 30, 2017.

(30) Foreign Application Priority Data
Aug. 31, 2016 (JP) .............................. JP2016-169609

(51) Int. Cl.
*G06K 9/00* (2022.01)
*G06T 7/70* (2017.01)
(Continued)

(52) U.S. Cl.
CPC ................ *G06T 7/70* (2017.01); *A61B 5/055* (2013.01); *A61B 6/03* (2013.01); *A61B 8/14* (2013.01);
(Continued)

(58) Field of Classification Search
None
See application file for complete search history.

(56) References Cited

U.S. PATENT DOCUMENTS

| | | | |
|---|---|---|---|
| 10,032,077 B1* | 7/2018 | Chow | ........................ G06T 7/60 |
| 2009/0074276 A1 | 3/2009 | Doi | |
| 2010/0054622 A1* | 3/2010 | Adams | ....................... G06T 7/13 |
| | | | 382/269 |

FOREIGN PATENT DOCUMENTS

| | | | |
|---|---|---|---|
| CN | 1628325 A | 6/2005 |
| JP | 2008108045 A | 5/2008 |

OTHER PUBLICATIONS

Aiko Sugimoto; Shigehiko Katsuragawa; Yoshikazu Uchiyama; and Junji Shiraishi; "Development of Temporal Subtraction Method for Chest Radiographs by Using Pixel Matching Technique;" Graduate School of Health Sciences, Kumamoto University, vol. 69, No. 8, Aug. 2013, pp. 1-9.

(Continued)

*Primary Examiner* — Sean M Conner
(74) *Attorney, Agent, or Firm* — Canon U.S.A., Inc. IP Division

(57) ABSTRACT

An image processing apparatus includes search area calculation means for calculating a search area size on the basis of a pixel size of at least one image among a first image and a second image, position obtaining means for obtaining a position of interest on the first image and a correspondence position on the second image corresponding to the position of interest, search area setting means for setting a search area made up of the search area size in a surrounding of the correspondence position on the second image, and difference means for deciding a difference value corresponding to the position of interest on a basis of a density value of the position of interest on the first image and density values of a plurality of positions in the search area on the second image.

16 Claims, 12 Drawing Sheets

(51) Int. Cl.
        A61B 8/14        (2006.01)
        G06T 7/00        (2017.01)
        A61B 6/03        (2006.01)
        G06T 5/50        (2006.01)
        A61B 5/055       (2006.01)
        G06T 1/00        (2006.01)
        G01T 1/161       (2006.01)
        G06T 5/00        (2006.01)

(52) U.S. Cl.
        CPC ............... *G01T 1/161* (2013.01); *G06T 1/00*
                (2013.01); *G06T 5/002* (2013.01); *G06T 5/50*
                (2013.01); *G06T 7/00* (2013.01); *G06T 7/97*
                (2017.01); *G06T 2207/20224* (2013.01)

(56)            References Cited

OTHER PUBLICATIONS

Yoshinori Itai; Hyoungseop Kim; Seiji Ishikawa; Shigehiko Katsuragawa; and Kunio Doi: "A Method for Reducing of Subtraction Artifacts in Temporal Subtraction Image Based on Voxel Matching Method," Institute of Electronics, Information and Communication Engineers (IEICE) Technical Report 2008, pp. 1-4.

Stan Birchfield and Carlo Tomasi; "A Pixel Dissimilarity Measure That Is Insensitive to Image Sampling" IEEE Transactions On Pattern Analysis and Machine Intelligence, vol. 20, No. 4, Apr. 1998, pp. 401-406.

Yoshinori Itai; Hyoungseop Kim; Seiji Ishikawa; Shigehiko Katsuragawa; and Kunio Doi "Development of a Voxel-Matching Technique for Substantial Reduction of Subtraction Artifacts in Temporal Subtraction Images Obtained from Thoracic MDCT," Journal of Digital Imaging vol. 23, No. 1, Feb. 2010, pp. 31-38.

Wei Jia;" The Study of Key Techniques of Palmprint Recognition;" University of Science and Technology of China; A Dissertation for Doctor's degree; Jul. 15, 2009; pp. 1-146.

Aoki T; "Temporal Subtraction Method for Lung Nodule Detection on Successive Thoracic CT Soft-Copy Images;" Apr. 30, 2014; Radiology: vol. 271: No. 1—Apr. 2014; radiology.rsna.org; pp. 255-261.

\* cited by examiner

IMAGE PROCESSING APPARATUS, IMAGE PROCESSING METHOD, AND PROGRAM

CROSS-REFERENCE TO RELATED APPLICATIONS

This application is a Continuation of International Patent Application No. PCT/JP2017/031194, filed Aug. 30, 2017, which claims the benefit of Japanese Patent Application No. 2016-169609, filed Aug. 31, 2016 and Japanese Patent Application No. 2017-165126, filed Aug. 30, 2017, both of which are hereby incorporated by reference herein in their entirety.

TECHNICAL FIELD

The disclosure of the present specification relates to an image processing apparatus, an image processing method, and a program.

BACKGROUND ART

In a medical field, a doctor conducts a diagnosis by using medical images captured by various modalities. In particular, for a follow-up examination of a state of a subject, the doctor contrasts a plurality of images captured by the same modality at different times with each other to perform an observation on a change over time of the subject. In a field other than the medical field too, in a case where a change over time of an object is examined, a similar operation may be implement in some cases. In addition, other than a comparison over time too, a diagnosis may be performed by contrasting two images obtained by capturing the same subject under different contrast conditions and different imaging parameters with each other in some cases. It should be noted that, hereinafter, one of images to be compared will be referred to as a first image, and the other image will be referred to as a second image.

An image subtraction technology has been proposed for assisting a contrast between images by performing registration of the first image and the second image to display a subtraction image in which a subtraction between those images is visualized. However, an issue occurs that noise is generated on the subtraction image due to an error in the registration or a subtraction between density values at the same site between the images. As countermeasures against the above-described issue, NPL 1 discloses a technology (voxel matching method) for obtaining each of subtractions between a pixel of interest on the first image and a pixel on the corresponding second image and its neighboring pixels and setting a lowest value among those subtractions as a density value of the subtraction image. According to this, since a pixel having a value closest to that of the pixel of interest is selected from the surrounding of the corresponding pixel and a subtraction value from the selected pixel is adopted, it is possible to reduce the noise on the subtraction image.

CITATION LIST

Non Patent Literature

NPL 1 Yoshinori Itai, Hyoungseop Kim, Seiji Ishikawa, Shigehiko Katsuragawa, Kunio Doi, "Development of a voxel-matching technique for substantial reduction of subtraction artifacts in temporal subtraction images obtained from thoracic MDCT." Journal of digital imaging, vol. 23, No. 1, pp. 31-38, 2010.

However, according to NPL 1, an issue occurs that the noise cannot be sufficiently reduced in some cases, or on the contrary, a necessary signal is also deleted in some cases. It should be noted that, without being limited by the above-described issue, attaining of actions and effects derived from respective configurations illustrated in embodiments for carrying out the invention described below which are not obtained by a related art can also be positioned as one of other issues in the present disclosure.

SUMMARY OF INVENTION

An image processing apparatus disclosed in the present specification includes image obtaining means for obtaining a first image and a second image in which a subject is captured, search area calculation means for calculating a search area size on a basis of a pixel size of at least one image among the first image and the second image, position obtaining means for obtaining a position of interest on the first image and a correspondence position on the second image corresponding to the position of interest, search area setting means for setting a search area made up of the search area size in a surrounding of the correspondence position on the second image, and subtraction means for deciding a subtraction value corresponding to the position of interest on a basis of a density value of the position of interest on the first image and density values of a plurality of positions in the search area on the second image.

Further features of the present invention will become apparent from the following description of exemplary embodiments with reference to the attached drawings.

BRIEF DESCRIPTION OF DRAWINGS

The accompanying drawings are included in the specification to constitute its part and illustrate embodiments of the present invention, and the accompanying drawings are used for describing a principle of the present invention together with its descriptions.

DESCRIPTION OF EMBODIMENTS

Hereinafter, preferred embodiments of an image processing apparatus according to the disclosure of the present specification will be described in detail in accordance with the accompanied drawings. It should be noted however that the scope of the invention is not to be limited to illustrated examples.

EMBODIMENTS

First Embodiment

The image processing apparatus according to the present embodiment is an apparatus that generates a three-dimensional subtraction image between a plurality of three-dimensional image (a first image and a second image). To calculate a subtraction at fine parts between the images, the image processing apparatus according to the present embodiment obtains a first converted image and a second converted image in which a resolution of each of the first image and the second image is converted such that a pixel size (voxel size) becomes different from the original image. Then, a position of interest on a first converted image and a correspondence position on the second converted image corresponding thereto are obtained, and a search area is set on the second converted image while the correspondence position is set as a center. At this time, by using a state in which positions of the pixels where an original imaging signal is most reflected by a displacement of discretized positions between images to be compared with each other are displaced by a size of half of the pixel at maximum, a size of the search area is calculated on the basis of the pixel size of each of the first image and the second image before the resolution is converted. Then, a subtraction in the position of interest is calculated on the basis of a density value of the position of interest on the first converted image and density values of the plurality of pixels in the search area set in the surrounding of the corresponding position on the second converted image, and a three-dimensional subtraction image in which the value is set as a density value of the position of interest on the three-dimensional subtraction image. According to this, when the subtraction value is calculated from the search area having the necessary minimum size, the user can examine the three-dimensional subtraction image in which the noise caused by the displacement of the discretized positions is reduced while a signal necessary to a diagnosis such as a subtraction based on changes over time is not deleted as much as possible. Hereinafter, a configuration and processing according to the present embodiment will be described by using FIG. 1 to FIG. 4.

Figure 1:
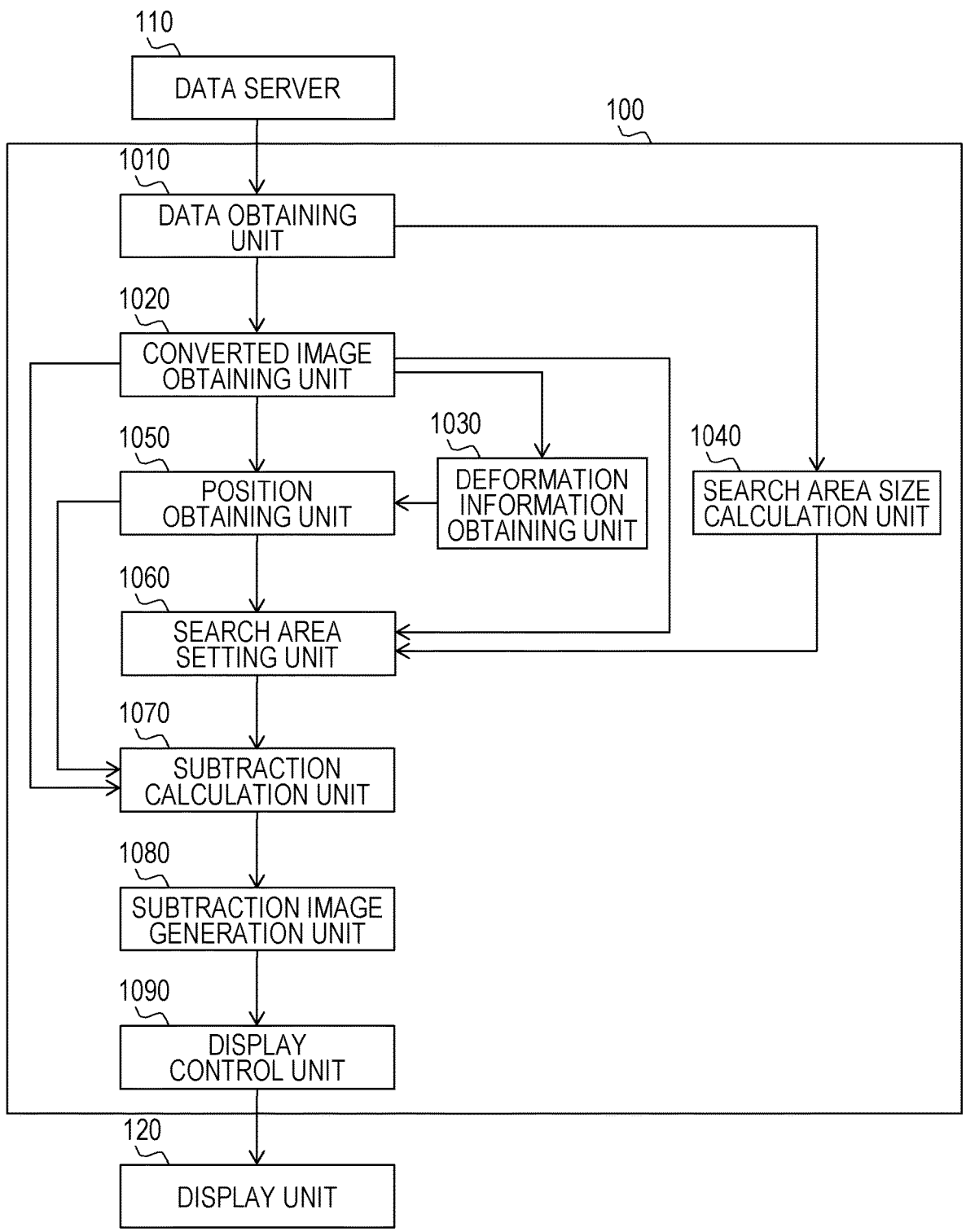
FIG. 1 illustrates an example of a device configuration of an image processing apparatus according to a first embodiment.

FIG. 1 illustrates a configuration of an image diagnosis system according to the present embodiment. As illustrated in the same drawing, an image processing apparatus 100 according to the present embodiment is connected to a data server 110 and a display unit 120.

The data server 110 holds the first image and the second image specified by a user as targets where the subtraction image is to be generated. The first image and the second image are three-dimensional tomography images (volume data) obtained by previously capturing a subject under different conditions (such as dates and times, contrast conditions, imaging parameters) in the same modality. The modality that captures the three-dimensional tomography images may be an MRI apparatus, an X-ray CT apparatus, a three-dimensional ultrasonic imaging apparatus, a photoacoustic tomography apparatus, a PET/SPECT, an OCT apparatus, or the like. In addition, the first image and the second image may be images in which the same patient is captured in the same modality with the same body posture in different dates and times for a follow-up examination or images in which the same patient is captured in different contrast conditions and different imaging parameters. In addition, the first image and the second image may be images in which different patients are captured or an image of a patient and a standard image. The first image and the second image are input to the image processing apparatus 100 via a data obtaining unit 1010.

The display unit 120 is a monitor that displays an image generated by the image processing apparatus 100.

The image processing apparatus 100 is constituted by the following components. The data obtaining unit 1010 obtains the first image and the second image input to the image processing apparatus 100. A converted image obtaining unit 1020 obtains a first converted image and a second converted image in which respective resolutions of the first image and the second image are converted. A deformation information obtaining unit 1030 obtains deformation information representing a correspondence relationship between positions on the images of the first converted image and the second converted image. A search area size calculation unit 1040 calculates a search area size on the basis of a pixel size of each of the first image and the second image. A position obtaining unit 1050 obtains the position of interest on the first converted image and obtains the correspondence position on the second converted image corresponding to the position of interest on the first converted image by using the deformation information obtained by the deformation information obtaining unit 1030. A search area setting unit 1060 sets a search area made up of the search area size in a surrounding of the correspondence position on the second converted image. A subtraction calculation unit 1070 calculates a subtraction value in the position of interest on the basis of the density value of the pixel of interest on the first converted image and the density values of the plurality of pixels in the search area on the second converted image. A subtraction image generation unit 1080 generates a subtraction image in which the calculated subtraction value is set as the density value of the position of interest. A display control unit 1090 performs display control for arranging the first image, the second image, and the subtraction image to be displayed by the display unit 120.

Figure 2:
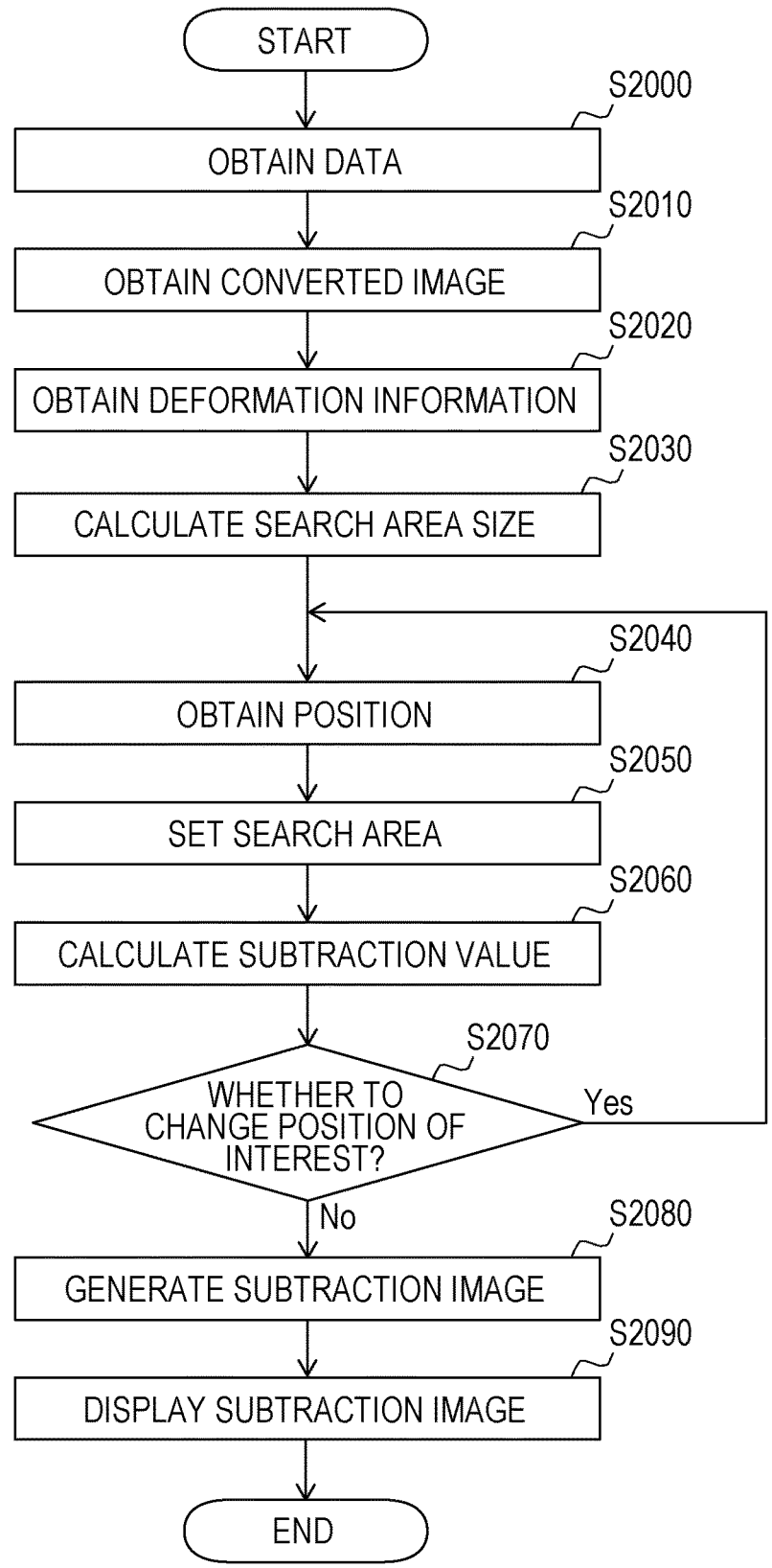
FIG. 2 is a flow chart illustrating an example of an overall processing procedure according to the first embodiment.

FIG. 2 illustrates a flow chart of an overall processing procedure performed by the image processing apparatus 100.

(S2000) (Obtainment of Data)

In step S2000, the data obtaining unit 1010 obtains the first image and the second image input to the image processing apparatus 100. Then, the obtained first image and the obtained second image are output to the converted image obtaining unit 1020. In addition, information related to the pixel sizes of the first image and the second image is output to the search area size calculation unit 1040.

(S2010) (Obtainment of Converted Image)

In step S2010, the converted image obtaining unit 1020 obtains the first converted image in which the resolution is converted such that the first image has a different pixel size and the second converted image in which the resolution is converted such that the second image has a different pixel size. For example, in a case where the pixel size of the original image is anisotropic, an image in which the pixel size becomes isotropic is obtained such that the registration between the images which will be performed in subsequent processing can be implemented at a high accuracy. For example, in a case where the first image and the second image are general CT images, since an in-slice plane resolution is high with respect to a distance between slices, up-sampling processing is performed on pixels in an intra-slice direction in accordance with the in-slice plane resolution. Similarly, in a case where the pixel sizes of the first image and the second image are not matched with each other, processing for converting the resolution of at least one of the images such that the pixel sizes of the respective images are set to be matched with each other. Normally, the conversion is performed such that the resolution is matched to the image having the higher resolution. Then, the generated converted image is output to the deformation information obtaining unit 1030, the position obtaining unit 1050, the search area setting unit 1060, and the subtraction calculation unit 1070.

It should be noted that, in a case where the resolution conversion processing is not necessary (for example, a case where the pixel sizes of the first image and the second image are isotropic and also equal to each other), the processing in the present step is not implemented, and the subsequent processing is executed while the original image is regarded as the converted image.

It should be noted that, according to the present embodiment, a related-art image processing technique can be used for an interpolation of the density value at the time of the resolution conversion. For example, a nearest neighbor interpolation, a linear interpolation, a cubic interpolation, or the like can be used.

(S2020) (Obtainment of Deformation Information)

In step S2020, the deformation information obtaining unit 1030 obtains the deformation information such that the pixels representing the same site are substantially matched with each other between the first converted image and the second converted image. That is, registration processing between (deformation estimating processing) between the first converted image and the second converted image is performed. Then, the obtained deformation information is output to the position obtaining unit 1050. That is, the deformation information obtaining unit 1030 obtains the deformation information between a reference image and the second converted image when the first converted image is set as the reference image.

According to the present embodiment, the deformation information is obtained by a related-art image processing technique. For example, the deformation information is obtained by deforming one of the images such that a degree of image similarity between the images after the deformation is increased. A related-art method such as a generally used Sum of Squared Differences (SSD), mutual information contents, or cross-correlation coefficients can be used for the degree of image similarity. In addition, a related-art deformation model such as a deformation model based on a radial basis function like Thin Plate Spline (TPS), Free Form Deformation (FFD), and Large Deformation Diffeomorphic Metric Mapping (LDDMM) can be used as the deformation model of the image. It should be noted that, in a case where only subtractions in positions and orientations exist (or an approximation can be performed to that effect) between the first image and the second image, rigid registration between the images may be performed to obtain transformation parameters of the positions and the orientations as the deformation information. In addition, affine transformation parameters between the images may be obtained as the deformation information. In addition, in a case where the positional displacement between the images does not exist (or an approximation can be performed to that effect), the processing in the present step becomes unnecessary.

(S2030) (Calculation of Search Area Size)

In step S2030, the search area size calculation unit 1040 calculates the search area size used for the calculation of the subtraction value on the basis of the pixel size of the first image and the pixel size of the second image. Then, the calculated search area size is output to the search area setting unit 1060.

According to the present embodiment, a nature that the positions of the pixels where the original imaging signal of the subject is most reflected between the first converted image and the second converted image are displaced by the sum of half of the pixel size of each of the original images at maximum by the displacement of the discretized positions at the time of the image generation between the first image and the second image is used for the calculation of the search area size. That is, the sum of half of the pixel size of each of the first image and the second image is calculated as the search area size.

Figure 3A:
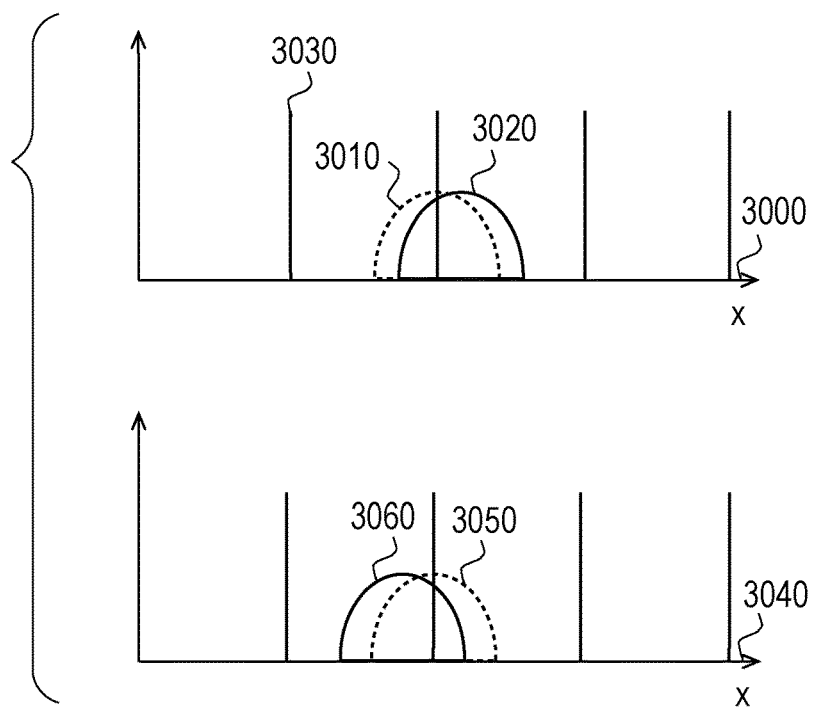
FIG. 3A illustrates an example of a displacement of discretized positions according to the first embodiment.

FIG. 3 are explanatory diagrams for describing a situation where a deviation is generated in observed values in the same site of the subject by the displacement of the discretized positions between the images. In FIG. 3A, graphic representations 3000 and 3040 represent appearing manners of the captured signal in a case where a capturing position of the subject is displaced in an opposite direction with respect to each of the modalities, in which the vertical axis indicates a signal value when the subject is captured by the modality, and the horizontal axis indicates a position in an x-axis direction. 3020 and 3060 denote signals obtained by capturing the same subject, and 3010 and 3050 represented by dotted lines indicate the same position on an x axis. Herein, 3010 and 3050 are signals in a case where the capturing is performed at the same position, and the position is referred to as a reference position for convenience herein. In FIG. 3A, it is represented that, when the images are generated from the signals 3020 and 3060 obtained from the same subject, each of discretized positions is displaced in different directions with respect to the reference position. In addition, lines 3030 arranged at an equal interval in FIG. 3A are boundary positions for discretization, and when the image is to be generated, the signals denoted by 3020 and 3060 are pulled together in an area sectioned by the lines to generate a single pixel.

Figure 3B:
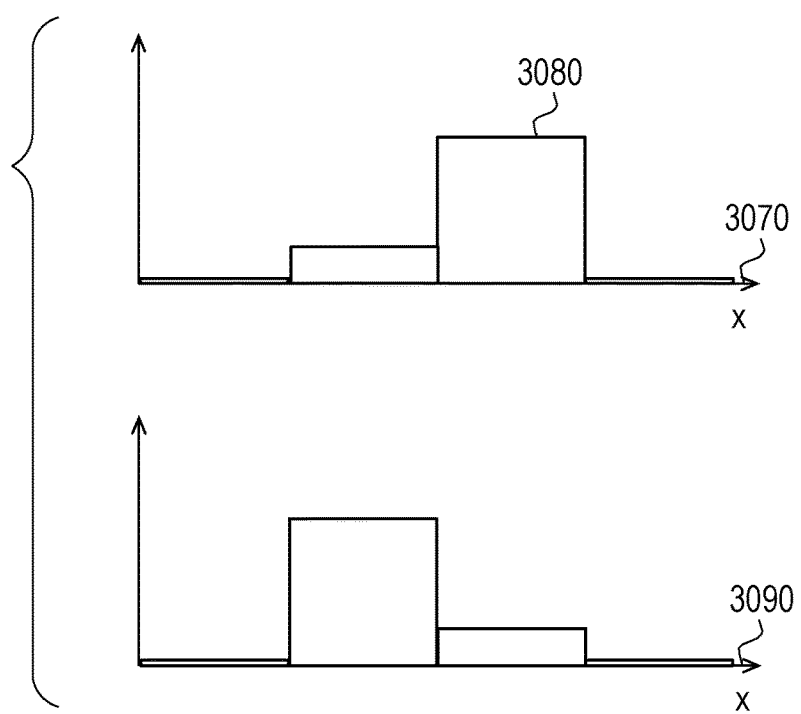
FIG. 3B illustrates an example of the displacement of the discretized positions according to the first embodiment.

In FIG. 3B, a graphic representation 3070 represents the information of the pixel generated by discretizing the signal 3020 of FIG. 3A, in which the vertical axis indicates a density value, and the horizontal axis indicates a position in the x-axis direction. For example, a pixel 3080 in FIG. 3B is a pixel generated from an area where a large number of the signals 3020 are included and represents that the density value is high. Similarly, in FIG. 3B, a graphic representation 3090 represents the information of the pixel generated by discretizing the signal 3060, in which the vertical axis indicates the density value, and the horizontal axis indicates the position in the x-axis direction. At this time, as described above, since the discretized positions of the signals 3020 and 3060 are displaced in mutually different directions, the density values in the same position vary between the graphic representations 3070 and 3090.

Figure 3C:
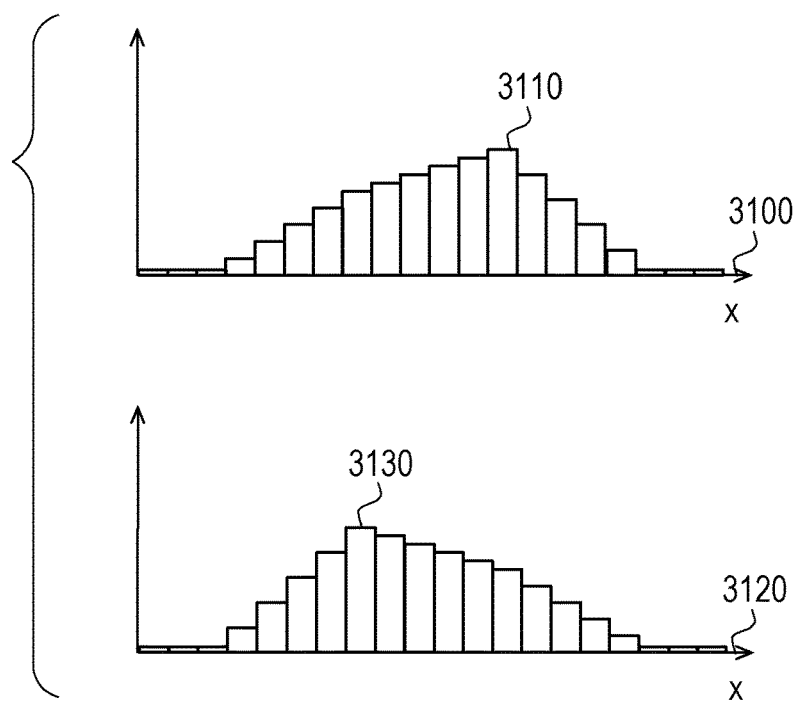
FIG. 3C illustrates an example of the displacement of the discretized positions according to the first embodiment.

In FIG. 3C, graphic representations 3100 and 3120 respectively represent density values and positions of the pixels in which the resolution conversion of the pixels represented by the graphic representation 3070 and the graphic representation 3090 in FIG. 3B is performed. That is, the graphic representations 3070 and 3090 can be regarded as the signal values of the first image and the second image, and the graphic representations 3100 and 3120 can be regarded as the signal values of the first converted image and the second converted image. At this time, pixels 3110 and 3130 are respectively pixels where the signals 3020 and 3060 of the subject are most reflected. In a case where the signals 3020 and 3060 are displaced in opposite directions, the displacements in the discretized positions of the signals with respect to the reference positions 3010 and 3050 are half the pixel size of the original image at maximum. In a case where the signals 3020 and 3060 are displaced in the opposite directions by half the pixel size, the displacement between the pixels 3110 and 3130 corresponds to the sum of half the pixel size each.

It should be noted that, in FIG. 3, the one-dimensional graphic representation in only the x-axis direction is used to simplify the illustration in the drawing, but in the actual three-dimensional image, since the discretized position is displaced in each of the x, y, and z-axis directions in some cases, the search area size is calculated on the basis of the pixel size in each of the axis directions. It should be noted that, since the in-slice resolution (pixel sizes in the x and y-axis directions) in the general CT image is sufficient in many cases, a configuration may be adopted in which the noise reduction is not performed with regard to the x and y-axis directions. In this case, the search area sizes in the x and y-axis directions may be set as 0, and only the search area size in the z-axis direction may be calculated by the above-described method. In addition, the search area sizes in the x and y-axis directions may be set as a predetermined fixed value (for example, 1 mm), and only the search area size in the z-axis direction may be calculated by the above-described method. According to this, it is possible to accelerate the calculation.

According to the present embodiment, the search area size is set as the sum of half of the pixel size of each of the first image and the second image, but the sum of the pixel size of each of the first image and the second image may be multiplied with a predetermined constant (for example, an expected value of the displacement of the discretized positions) or may be calculated on the basis of a pixel size of at least one image among the first image and the second image. In addition, the above-described predetermined constant may be changed on the basis of the registration technique for the first image and the second image. For example, when the registration is performed such that the subtraction in the density values between the images becomes lower, the positional displacement of the pixels by the displacement of the discretized positions is corrected, and the positions of the pixels representing the same site between the images are set to be closer to each other in some cases. For this reason, the above-described predetermined constant may be decreased, and the search area size may be set to be smaller than the maximum value the displacement of the discretized positions. According to this, the search area size becomes smaller, and the subtraction in the excessive range is not calculated, so that a processing speed and an accuracy can be improved.

In addition, according to an registration technique for decreasing a distance of the corresponding positions (feature points) between the images instead of the subtraction in the density values, the positional displacement of the pixels by the displacement of the discretized positions is not necessarily decreased. In general, an registration accuracy in the surrounding of the feature points between the images used for the registration is high, and the registration accuracy is lower as being away from the feature points. In a case where the registration accuracy is low, the positional displacement of the pixels between the images may be increased in some cases while an registration error is added to the displacement of the discretized positions. In the above-described case, in accordance with the distance on the image to the feature point, the above-described predetermined constant may be changed for each position on the image. For example, the above-described predetermined constant may be decreased in the position in the surrounding of the feature point on the image, and the above-described predetermined constant may be increased in the position away from the feature point.

(S2040) (Obtainment of Position)

In step S2040, the position obtaining unit 1050 obtains the position of interest on the first converted image (position of interest on the reference image) and obtains the correspondence position on the second converted image corresponding to the position of interest by using the deformation information obtained in step S2020. Then, the obtained positions are output to the search area setting unit 1060 and the subtraction calculation unit 1070.

(S2050) (Setting of Search Area)

In step S2050, the search area setting unit 1060 sets the search area made up of the search area size calculated in step S2030 in the surrounding while the correspondence position on the second converted image is set as the center. Then, the information of the set search area is output to the subtraction calculation unit 1070.

Figure 4:
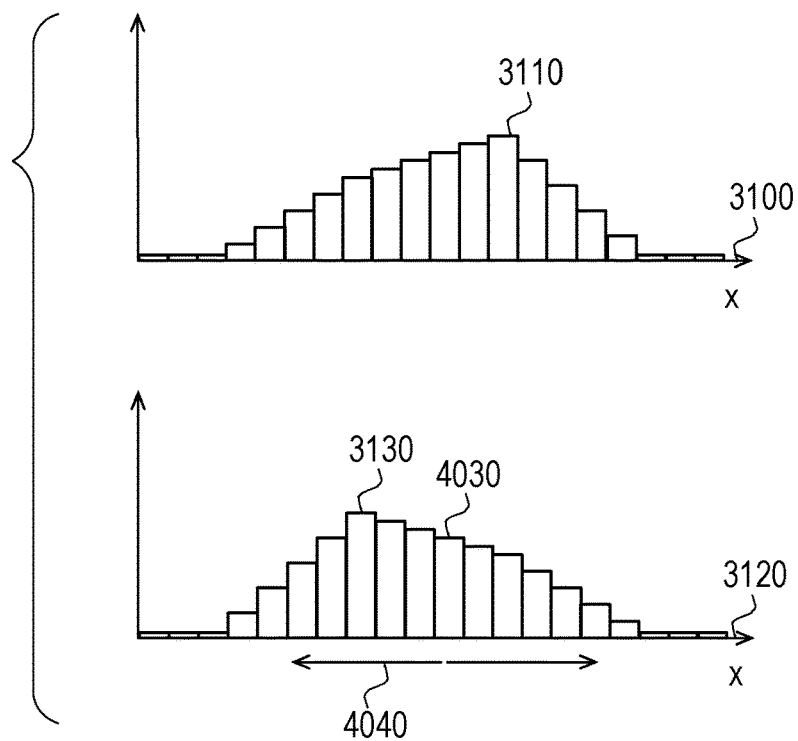
FIG. 4 is an explanatory diagram for describing an example of a setting method for a search area according to the first embodiment.

FIG. 4 is an explanatory diagram for describing the search area set on the converted image. In FIG. 4, the graphic representations 3100 and 3120 respectively represent the same graphic representations as the graphic representations 3100 and 3120 in FIG. 3C. Herein, an example of a case will be illustrated where the pixel sizes in the x-axis direction in the first image and the second image are both 5 mm, and up-sampling is performed such that the pixel sizes become 1 mm. In this case, since the search area size in the x-axis direction is the sum of half of the pixel size of each of the first image and the second image, 2.5 mm+2.5 mm=5 mm is established. In FIG. 4, when the pixel 3110 on the first converted image is set as the position of interest, it is assumed that the correspondence position corresponding to this (which is calculated on the basis of the deformation information) on the second converted image is a pixel 4030. At this time, 4040 denotes a search area having a size of 5 mm set in the pixel 4030 that is the correspondence position. A case where the discretized position is displaced in the x-axis direction by 5 mm at maximum is taken into account, and a search area of 5 mm in each of +x and −x directions is set while the pixel 4030 is set as the center. Herein, only the x-axis direction has been described to simplify the illustration in the drawing, but in the actual three-dimensional image, the search area is a rectangular search area made up of the search area size calculated on the basis of the pixel size in each of the x, y, and z-axis directions.

(S2060) (Calculation of Subtraction Value)

In step S2060, the subtraction calculation unit 1070 obtains the subtraction value assigned to the subtraction image on the basis of the density value of the position of interest on the first converted image and the density value of each of the pixels in the search area on the second converted image which are obtained in step S2040. For example, processing similar to the voxel matching described in NPL 1 is performed. That is, the subtraction between the density value of the position of interest on the first converted image and the density value of each of the pixels in the search area on the second converted image is calculated, and the minimum value among those is obtained as the subtraction value assigned to the subtraction image. That is, the subtraction calculation unit 1070 calculates the subtraction between the density value of the position of interest on the reference image and the density value of each of a plurality of positions in the search area on the second converted image. Then, the subtraction is output to the subtraction image generation unit 1080.

In FIG. 4, by obtaining the subtraction between the density value of the pixel 3110 of the first converted image and each density value in the search area on the second converted image 4040, the subtraction value with the pixel 3130 of the second converted image is obtained in which the subtraction with the pixel 3110 of the first subtraction image becomes the minimum value. That is, it is possible to calculate the subtraction value of the density values between the pixels where the signal of the subject is most reflected in FIG. 3.

According to the present embodiment, the pixels in the search area on the second converted image where the subtraction with the density value of the position of interest on the first converted image is calculated may be all the pixels in the search area. Alternatively, the pixels may be pixels sampled in the search area at a predetermined interval or pixels randomly sampled by a predetermined number of pixels. In addition, the pixels may be pixels in a spherical area inscribed with the search area. According to this, the number of time to calculate the subtraction is reduced, and the processing can be accelerated.

In addition, as another method using the value of the subtraction between the density value of the position of interest on the first converted image and the density value of each of the pixels in the search area on the second converted image, an average value of the subtractions or a second lowest subtraction instead of the minimum value of the subtractions may be calculated to be set as the subtraction value of the subtraction image. According to this, while more noise remains than a case where the minimum value of the subtractions is obtained, the subtraction on the second converted image with the pixel of interest on the first converted image is small, but it is possible to prevent the obtainment of the subtraction with a pixel in a position that is not corresponding (such as an artifact or a pixel in another site) as the minimum value. According to this, it is possible to prevent a situation where the subtraction value becomes substantially lower than the subtraction with the pixel in the originally corresponding position.

In addition, distribution information of the density values in the search area on the second converted image may be calculated, and the subtraction value may be obtained by the comparison between the distribution information and the density value of the position of interest on the first converted image. For example, the maximum value and the minimum value of the density values may be obtained as a density range of the density values in the search area, and the subtraction value may be obtained by the comparison with the density value of the position of interest on the first converted image. For example, when the density value of the position of interest is in between the maximum value and the minimum value of the density values in the search area, 0 may be set as the subtraction value assigned to the subtraction image. In a case where the density value is higher than the maximum value, a subtraction value with the maximum value may be set as the subtraction value assigned to the subtraction image. In a case where the density value is lower than the minimum value, a subtraction value with the minimum value may be set as the subtraction value assigned to the subtraction image. Alternatively, when the density value is in between the maximum value and the minimum value, 0 may be set as the subtraction value assigned to the subtraction image, and otherwise, the minimum value of the subtractions with each the density values in the search area may be set as the subtraction value assigned to the subtraction image. At this time, the maximum value and the minimum value of the density values in the search area on the second converted image represent a range where the density value in the position of interest on the first converted image may change by the subtraction in the discretized positions. For this reason, even in a case where the density values at the same site between the images are not completely matched with each other because of the influence of the discretization to remain as a slight subtraction, the subtraction can be set as 0 within a range that may be changed by the subtraction in the discretized positions, and the noise can be further reduced. It should be noted that the density range in the search area may be a range other than the maximum value and the minimum value of the density values. For example, the density range may be a maximum value and a minimum value after outliers of the density values are removed.

However, in a case where a pixel in which a density value largely varies by a lesioned part or an artifact is included in the search area, a width of the maximum value and the minimum value of the density values in the search area is increased, and the subtraction of the position of interest may be erroneously set as 0 in some cases. For this reason, the subtraction may be set as 0 in only a position where the density value of the position of interest is in between the maximum value and the minimum value of the density values in the search area and also the subtractions between the density value of the position of interest and the maximum value and the minimum value are lower than or equal to a threshold. Alternatively, the distribution of the density values in the search area may be classified into a plurality of clusters, and similar processing to the above-described processing may be performed on the basis of the comparison between the minimum values and the maximum values in the respective clusters. That is, in a case where the density value of the position of interest is within the cluster, 0 may be set as the subtraction value, and in a case where the density value of the position of interest is out of the cluster, a (signed) distance to the closest cluster may be set as the subtraction value. It should be noted that the classification of the density values in the search area may be performed on the basis of only the density value or may also be performed on the basis of the pixel position and the density value. In the former case, for example, clustering processing may be applied to a histogram of the density values in the search area. In the latter case, for example, clustering can be performed by applying area division processing into the search area on the basis of a continuity of the density values between the pixels.

In addition, according to the present embodiment, the search area may be set in the surrounding while the original correspondence position on the second image is set as the center instead of the setting on the second converted image, and the subtraction between the density value in the position of interest on the first converted image and the density value in the search area on the second image may be calculated. At this time, density values of a plurality of positions in the search area may be obtained at an interval smaller than the pixel size. The density values in these positions are obtained by performing an interpolation from the surrounding density value. When an interpolation method is similar to the case when the second converted image is obtained in step S2010, it is possible to calculate the subtraction value equivalent to a case where the search area is set on the second converted image.

In addition, the subtraction value obtained on the basis of the density value of the position of interest on the first converted image and the density value of each of the pixels in the search area on the second converted image as described above may be set as a first subtraction value, and a subtraction (second subtraction value) between the density value of the position of interest on the first converted image and the density value of the correspondence position on the second converted image may be separately obtained, so that the subtraction value assigned to the subtraction image may be calculated on the basis of the first subtraction value and the second subtraction value. For example, a weighted average value of the first subtraction value and the second subtraction value can be set as the subtraction value of the subtraction image. According to this, it is possible to reduce the risk that the signal that is not the noise is to be deleted.

(S2070) (Whether to Change Position of Interest?)

In step S2070, the position obtaining unit 1050 determines whether or not the subtraction values in all the positions (all the pixels) on the first converted image are calculated. In a case where the subtraction values in all the positions are calculated, the processing proceeds to step S2080. On the other hand, in a case where the subtraction values in all the positions are not obtained, the processing returns to step S2040.

It should be noted that, according to the present embodiment, the positions where the calculation of the subtraction value is to be performed may be part of positions on the first converted image previously extracted by the related-art image processing technology instead of all the positions on the first converted image. According to this, it is possible to reduce the processing time necessary for the noise reduction.

(S2080) (Generation of Subtraction Image)

In step S2080, the subtraction image generation unit 1080 generates the subtraction image (the first subtraction image) in which the subtraction value in each of the positions on the first converted image is set as the density value. Then, the obtained subtraction image is saved in the data server 110. In addition, the obtained subtraction image is output to the display control unit 1090. It should be noted that a general subtraction image (second subtraction image) in which the second subtraction value (subtraction between the density value of the position of interest on the first converted image and the density value of the correspondence position on the second converted image) which is calculated in step S2060 is set as the density value may also be generated as well.

(S2090) (Display of the Subtraction Image)

In step S2090, the display control unit 1090 performs control for displaying the subtraction image generated in step S2080 (the first subtraction image) on the display unit 120.

As an example of the display, a single screen, for example, may be vertically or horizontally divided to arrange each of the first image, the second image, and the subtraction image to be displayed. The subtraction image (the first subtraction image) drawn in a different color from the first image or the second image may be overlapped to be displayed. Only one of the first image, the second image, and the subtraction image may be selected, and the display can be performed (while being freely switched in the same position). In addition, in accordance with a resolution of one of the images, the other image may be expanded or reduced to be displayed. Each of the images may be arranged to be displayed such that the correspondence position on the second image corresponding to the single position of interest on the first image and the position in interest of the subtraction image are aligned with each other. In addition, the first subtraction image and the second subtraction image may be switched, so that the display can be performed.

In the above-described manner, the processing of the image processing apparatus 100 is implemented.

As described above, when the subtraction value is calculated from the search area having the necessary minimum size in which the displacement of the discretized positions is taken into account, the user can observe the subtraction image in which the necessary signal on the subtraction image is kept, and also the noise generated from the subtraction in the density values due to the displacement of the discretized positions between the images is reduced.

(Modified Example 1-1) (Calculation of Degree of Image Similarity in which Displacement of Discretized Positions is Taken into Account)

According to the present embodiment, when the subtraction between the pixels of interest is obtained, the technique for setting the search area having the size determined on the basis of the pixel size in the surrounding of the pixel and using the density value in the area is used for the noise reduction at the time of the subtraction image generation. However, this method can also be used in other situations where the comparison between the pixels of interest is performed. For example, in step S2020, the deformation information obtaining unit 1030 obtains the degree of image similarity by using the related-art image processing technique, but this method can also be used in the processing for obtaining the degree of image similarity for the image registration. That is, like the SSD, when the subtraction in the density values of a certain pixel pair between the images is calculated, the pixel pair may be arranged in the position of interest and the correspondence position, and the subtraction value may be calculated by processing similar to step S2050 and step S2060. In the registration where the deformation information is repeatedly optimized to increase the degree of image similarity, the degree of image similarity is evaluated which is obtained on the basis of the image in which the noise is reduced to be finally observed by the user in respective steps in the optimization and the subtraction value calculated in the similar steps. According to this, the degree of image similarity in which the displacement of the discretized positions is taken into account can be calculated, and as a result, it is possible to obtain the subtraction image in which the noise is further reduced.

(Modified Example 1-2) (Noise in Position Specified by User is Reduced)

According to the present embodiment, in step S2070, all the positions (all the pixels) on the first converted image or part of the positions previously extracted by the related-art image processing technology are used, but the user may specify the positions. That is, the generation processing for the subtraction image in which the noise is reduced may be performed while all the positions in the area previously specified by the user or part of the positions are set as the target. In addition, only the second subtraction image may be generated and displayed, and the processing in steps S2040 to S2080 may be applied in only the neighboring area of the position of interest which is interactively specified by the user to replace only the neighboring area with the first subtraction image to be displayed. According to this, when the noise in only the necessary minimum position is reduced, the time necessary for the noise reduction can be shortened. Furthermore, since it is possible to exclude the position where the user determines that it is not the noise from the target of the noise reduction processing, it is possible to prevent the excessive signal deletion.

Second Embodiment

The image processing apparatus according to the present embodiment is an apparatus that generates a three-dimensional subtraction image between the first image and the second image similarly as in the first embodiment. It is a feature that the image processing apparatus according to the present embodiment determines whether or not the noise reduction processing is to be executed in accordance with the pixel size of the input image and generates a three-dimensional subtraction image in accordance with the determined method. The image processing apparatus according to the present embodiment calculates the search area size on the basis of the pixel sizes of the first image and the second image similarly as in the first embodiment. At this time, in a case where the pixel sizes of the first image and the second image are lower than a predetermined threshold, it is determined that the displacement of the discretized positions is small, and the subtraction image is generated without implementing the noise reduction processing. On the other hand, in a case where the pixel sizes are higher than or equal to the predetermined threshold, the subtraction image in which the noise reduction processing has been implemented is generated similarly as in the first embodiment. According to this, in a case where the displacement of the discretized positions is small, it is possible to suppress the excessive deletion of the subtraction in the density values between the images. In addition, the processing time necessary for the noise reduction can be shortened. Hereinafter, a configuration and processing according to the present embodiment will be described by using FIG. 1 and FIG. 5.

A configuration of the image processing apparatus according to the present embodiment is similar to that of the first embodiment. However, since the search area size calculation unit 1040 and the subtraction calculation unit 1070 have the functions different from the first embodiment, the functions will be described below. With regard to the other configurations, since the functions are the same as the first embodiment, the descriptions thereof will be omitted.

The search area size calculation unit 1040 determines whether or not the noise reduction processing is to be implemented on the basis of the pixel sizes of the first image and the second image. In addition, similarly as in the first embodiment, the calculation of the search area size is performed on the basis of the pixel sizes of the first image and the second image. In a case where the noise reduction processing is not to be implemented, the subtraction calculation unit 1070 calculates the subtraction value between the density value of the position of interest on the first converted image and the density value of the correspondence position on the second converted image as the subtraction value in the position of interest. On the other hand, in a case where the noise reduction processing is to be implemented, processing similar to the first embodiment is performed.

Figure 5:
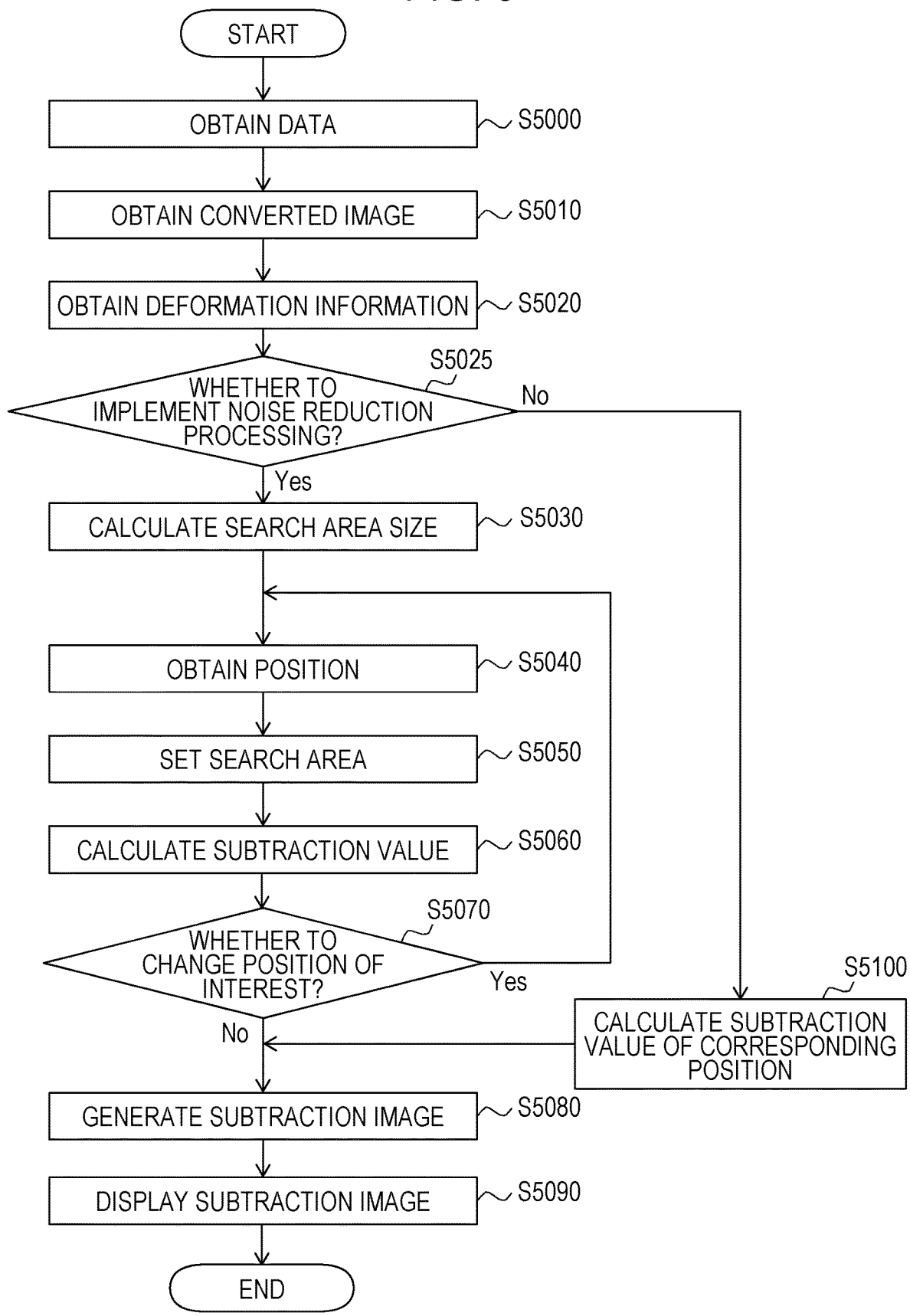
FIG. 5 is a flow chart illustrating an example of the overall processing procedure according to a second embodiment.

FIG. 5 illustrates a flow chart of the overall processing procedure performed by the image processing apparatus 100. In steps S5000 to S5020 and S5030 to S5090, since the processes respectively similar to step S2000 to S2020 and S2030 to S2090 according to the first embodiment are performed, the descriptions thereof will be omitted. Hereinafter, only a different part from the flow chart in FIG. 2 will be described.

(S5025) (Whether to Implement Noise Reduction Processing?)

In step S5025, the search area size calculation unit 1040 determines whether or not the noise reduction processing is to be implemented on the basis of the pixel sizes of the first image and the second image.

Herein, in a case where the pixel sizes of both the first image and the second image are lower than a predetermined threshold, it is determined that the displacement of the discretized positions is small to determine that the noise reduction is not necessary to be implemented, and the processing proceeds to step S5100. On the other hand, in a case where the pixel sizes are higher than or equal to the predetermined threshold, the processing proceeds to step S5030, and the noise reduction processing similar to the first embodiment is implemented. For example, a value in accordance with a lesion size or resolution power of the modality or a value previously decided by the user is set as the threshold.

According to the present embodiment, it is determined whether or not the noise reduction processing is to be implemented on the basis of the pixel size of each of the first image and the second image, but the determination may be performed on the basis of the sum of the pixel size of each of the first image and the second image. In addition, the predetermined threshold may be a different value in each of the x, y, and z-axis directions of the image. In addition, the determination on whether to perform the noise reduction or not may be performed for each axis to control whether to implement the noise reduction processing or not for each axis. For example, in a case where the pixel sizes in the x and y-axis directions of each of the first image and the second image are lower than the threshold and the pixel size in the z-axis direction is higher than or equal to the threshold, it may be determined that the noise reduction is not necessary in the x and y-axis directions to set the search area size as 0 and may also be determined that the noise reduction is necessary in only the z-axis direction to calculate the search area size similarly as in the first embodiment. Then, the processing proceeds to step S5100 in a case where it is determined that the noise reduction is not necessary in all the three axis directions, and the processing proceeds to step S5030 in other cases.

It should be noted that, since the in-slice resolution (=the pixel sizes in the x and y directions) in the general CT image is sufficient in many cases, a configuration may be adopted in which the noise reduction is not regularly performed without performing the determination based on the image size with regard to the x and y directions. That is, it may be determined whether or not the noise reduction in the z direction is to be performed on the basis of a slice interval of the input image (=the pixel size in the z direction). According to this, the determination can be performed such that the noise reduction is not performed in a case where the input image is a thin slice, and the noise reduction is performed in a case where the input image is a thick slice.

(S5100) (Calculation of Subtraction Value of Corresponding Position)

In step S5100, the subtraction calculation unit 1070 calculates the subtraction value of the density values (second subtraction value according to the first embodiment) in the corresponding position between the first converted image and the second converted image. At this time, the corresponding position between the images is obtained by using the deformation information similarly as in step S5040.

According to the present embodiment, when the determination on whether to perform the noise reduction processing or not is performed in accordance with the pixel size, in a case where the pixel size of the input image is sufficiently small and the noise based on the discretization is small, the unnecessary calculation can be omitted. In addition, as compared with the first embodiment, an advantage is attained that the excessive deletion of the original subtraction value is prevented.

Third Embodiment

The image processing apparatus according to the present embodiment is an apparatus that generates a three-dimensional subtraction image between the first image and the second image similarly as in the first embodiment. It is a feature that the image processing apparatus according to the present embodiment generates the three-dimensional subtraction image in which the noise is reduced by using a deformed search area where the search area is projected onto a deformed image in which deformation registration is performed such that the same sites between the images are substantially matched with each other. Similarly as in the first embodiment, the image processing apparatus according to the present embodiment obtains the first converted image and the second converted image in which each of the first image and the second image are converted such that the resolutions are different from the original image and sets the search area in the surrounding of the correspondence position on the second converted image corresponding to the position of interest on the first converted image. Then, the deformation registration of the second converted image is performed such that the density values of the respective pixels become similar to those of the first converted image and projects the search area onto the obtained second deformed converted image by using the deformation information. Then, the subtraction of the position of interest is calculated on the basis of the density value of the position of interest on the first converted image and the density values of the plurality of pixels in the deformed search area set in the surrounding of the correspondence position on a second deformed converted image, and the three-dimensional subtraction image in which the value is set as the density value of the position of interest on the three-dimensional subtraction image is generated. Since the deformed image of the second image in which the position of the same site on the image is substantially matched with the first image and the subtraction image can be obtained, when these images are arranged to be displayed, the user can easily check the density value in which positions on the first image and the deformed image the subtraction value on the subtraction image is calculated from. Hereinafter, a configuration and processing according to the present embodiment will be described by using FIG. 6 and FIG. 7.

Figure 6:
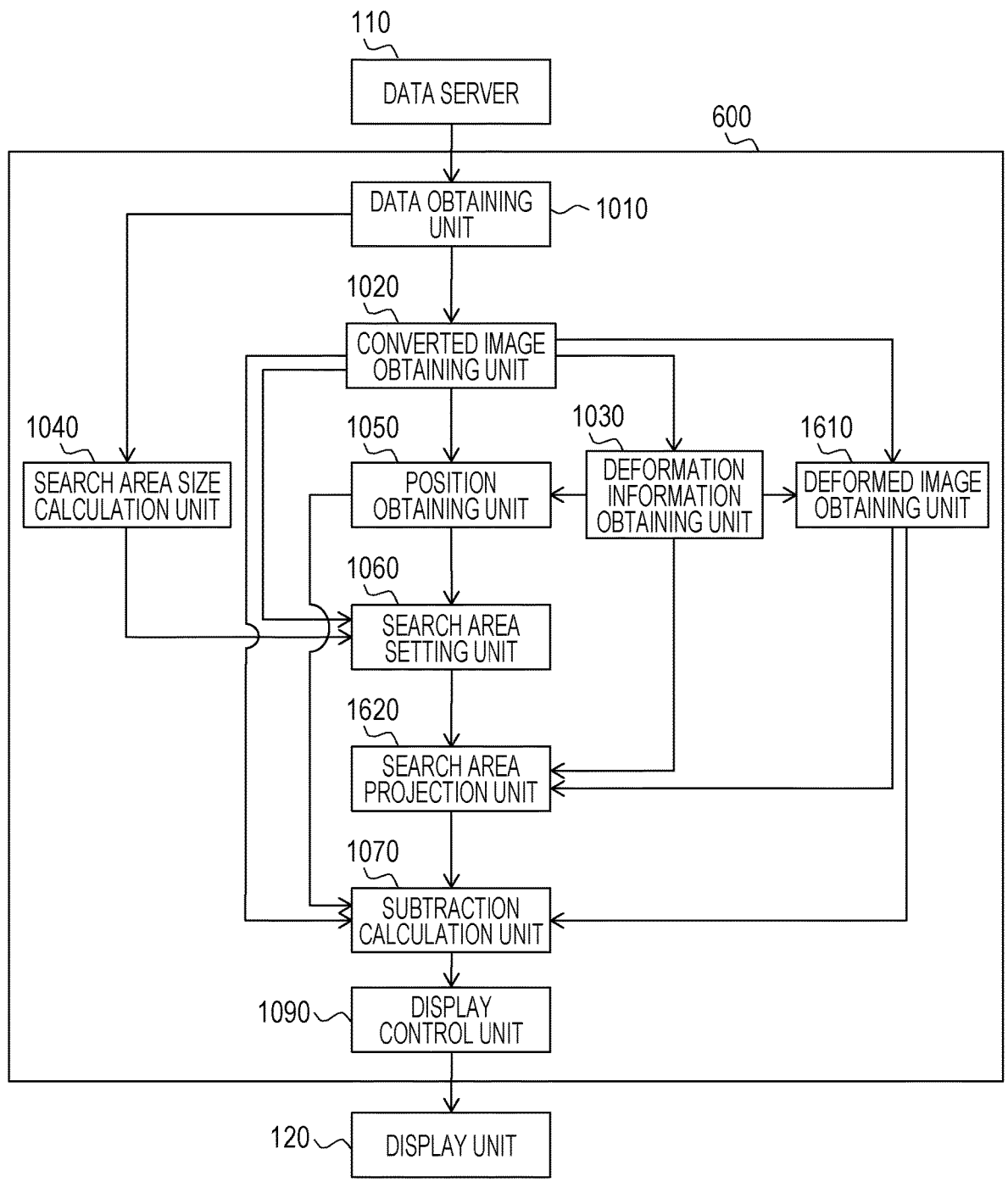
FIG. 6 illustrates an example of the device configuration of the image processing apparatus according to a third embodiment.

FIG. 6 illustrates a configuration of the image diagnosis system according to the present embodiment. Herein, since the data server 110 and the display unit 120 are similar to those of the first embodiment, the descriptions thereof will be omitted. An image processing apparatus 600 is constituted by the following components. Since the data obtaining unit 1010, the converted image obtaining unit 1020, the deformation information obtaining unit 1030, the search area size calculation unit 1040, the position obtaining unit 1050, the search area setting unit 1060, and the display control unit 1090 are the same functions as the first embodiment, the descriptions thereof will be omitted.

A deformed image obtaining unit 1610 obtains a second deformed converted image in which the second converted image is deformed by using the deformation information obtained by the deformation information obtaining unit 1030. A search area projection unit 1620 obtains the deformed search area by projecting the search area set on the second converted image by the search area setting unit 1060 onto the second deformed converted image by using the deformation information obtained by the deformation information obtaining unit 1030. The subtraction calculation unit 1070 calculates the subtraction value in the position of interest on the basis of the density value of the pixel of interest on the first converted image and the density values of the plurality of pixels in the deformed search area on the second deformed converted image.

Figure 7:
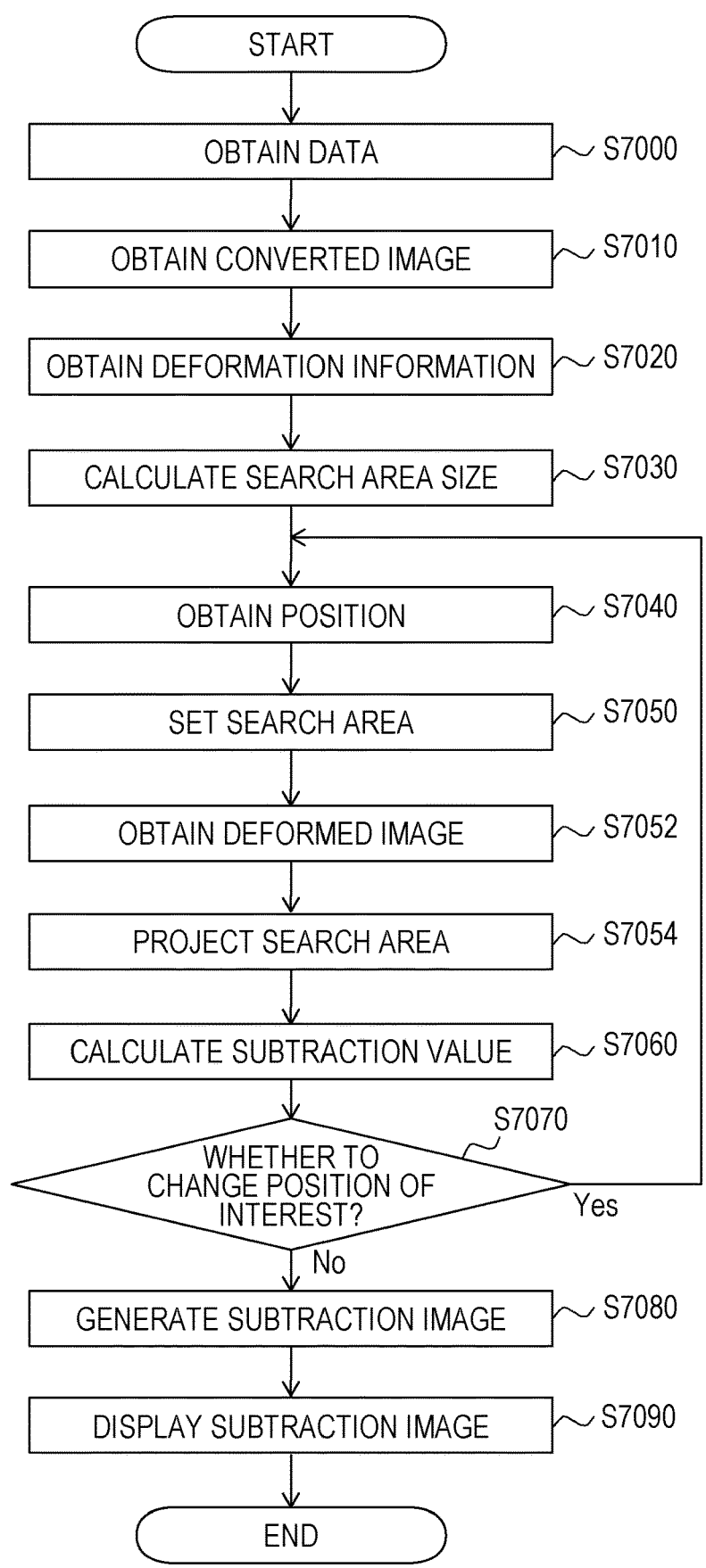
FIG. 7 is a flow chart illustrating an example of the overall processing procedure according to the third embodiment.

FIG. 7 illustrates a flow chart of the overall processing procedure performed by the image processing apparatus 600. In steps S7000 to S7050 and S7070 to S7090, since the processes respectively similar to step S2000 to S2050 and S2070 to 2090 according to the first embodiment are performed, the descriptions thereof will be omitted. Hereinafter, only a different part from the flow chart in FIG. 2 will be described.

(S7052) (Obtainment of Deformed Image)

In step S7052, the deformed image obtaining unit 1610 obtains the second deformed converted image in which the second converted image is deformed by using the deformation information obtained in step S7020. Then, the obtained second deformed converted image is output to the search area projection unit 1620 and the subtraction calculation unit 1070.

(S7054) (Projection of Search Area)

In step S7054, the search area projection unit 1620 projects the search area set on the second converted image in step S7050 onto the second deformed converted image as the deformed search area by using the deformation information obtained in step S7020. Then, the image is output to the subtraction calculation unit 1070.

Herein, the search area on the second converted image to be projected may be the entire area in the search area or may also be a plurality of positions sampled from the search area. In a case where the entire area in the search area is projected, an entire internal area of a contour of the search area projected onto the second deformed converted image by using the deformation information can be set as the deformed search area.

(S7060) (Calculation of Difference Value)

In step S7060, the subtraction calculation unit 1070 obtains the subtraction value assigned to the subtraction image on the basis of the density value of the position of interest on the first converted image which is obtained in step S7060 and the density value of each of the pixels in the deformed search area on the second deformed converted image which is projected in step S7054. A subtraction from the process in step S2060 according to the first embodiment is only that the second converted image is changed to the second deformed converted image and the search area is changed to the deformed search area, and the other processes are similar.

In the above-described manner, the processing of the image processing apparatus 600 is implemented.

According to the present embodiment, it is possible to perform the observation while the same sites between the deformed image of the second image in which the position of the same site on the image is substantially matched with the first image and the subtraction image in which the noise is reduced are easily compared with each other. For this reason, as compared with the first embodiment, an advantage is attained that the user can easily determine whether or not the subtraction value on the subtraction image is a subtraction based on the lesion.

(Modified Example 3-1) (Calculation of Degree of Image Similarity by Taking Displacement of Discretized Positions into Account)

Similarly as in the modified example 1-1 of the first embodiment, the degree of image similarity may be obtained on the basis of the subtraction value in which the noise caused by the displacement of the discretized positions is reduced when the degree of image similarity is calculated. Herein, the minimum value of the subtractions between the density value of the position of interest on the first converted image and each of the density values in the deformed search area on the second deformed converted image is used. According to this, the degree of image similarity in which the displacement of the discretized positions is taken into account can be obtained, and as a result, it is possible to obtain the subtraction image in which the noise is further reduced.

Fourth Embodiment

The image processing apparatus according to the present embodiment is an apparatus that generates the subtraction image between the three-dimensional images similarly as in the first embodiment. It is a feature that the image processing apparatus according to the present embodiment sets the search area in both the position of interest on the first converted image and the correspondence position on the second converted image and obtains the subtraction value in the position of interest on the basis of the density values of the pixels in each of the search areas. Herein, similarly as in the first embodiment, a direction in which the search area is set on the second converted image to obtain the subtraction with the position of interest on the first converted image is set as a forward direction. In addition, a direction in which the search area is set on the first converted image to obtain the subtraction with the correspondence position on the second converted image is set as a backward direction. The image processing apparatus according to the present embodiment obtains the subtraction value in the position of interest on the subtraction image in each of the forward direction and the backward direction and sets a representative subtraction value in which the two subtraction values are integrated with each other as the density value of the subtraction image to be generated. According to this, the signal that cannot be captured by the calculation in only one of the directions can be kept in the subtraction image. Hereinafter, a configuration and processing according to the present embodiment will be described by using FIG. 1 and FIG. 8.

A configuration of the image processing apparatus according to the present embodiment is similar to that of the first embodiment. However, since the search area setting unit 1060 and the subtraction calculation unit 1070 have different functions from the first embodiment, the functions will be described below. Since the functions of the other configurations are the same as the first embodiment, the descriptions thereof will be omitted.

The search area setting unit 1060 sets the search area made up of the search area size in each of the surrounding of the position of interest on the first converted image and the surrounding of the correspondence position on the second converted image. The subtraction calculation unit 1070 calculates each of the subtraction value in the forward direction and the subtraction value in the backward direction and obtains the representative subtraction value in which the two subtraction values are integrated with each other.

Figure 8:
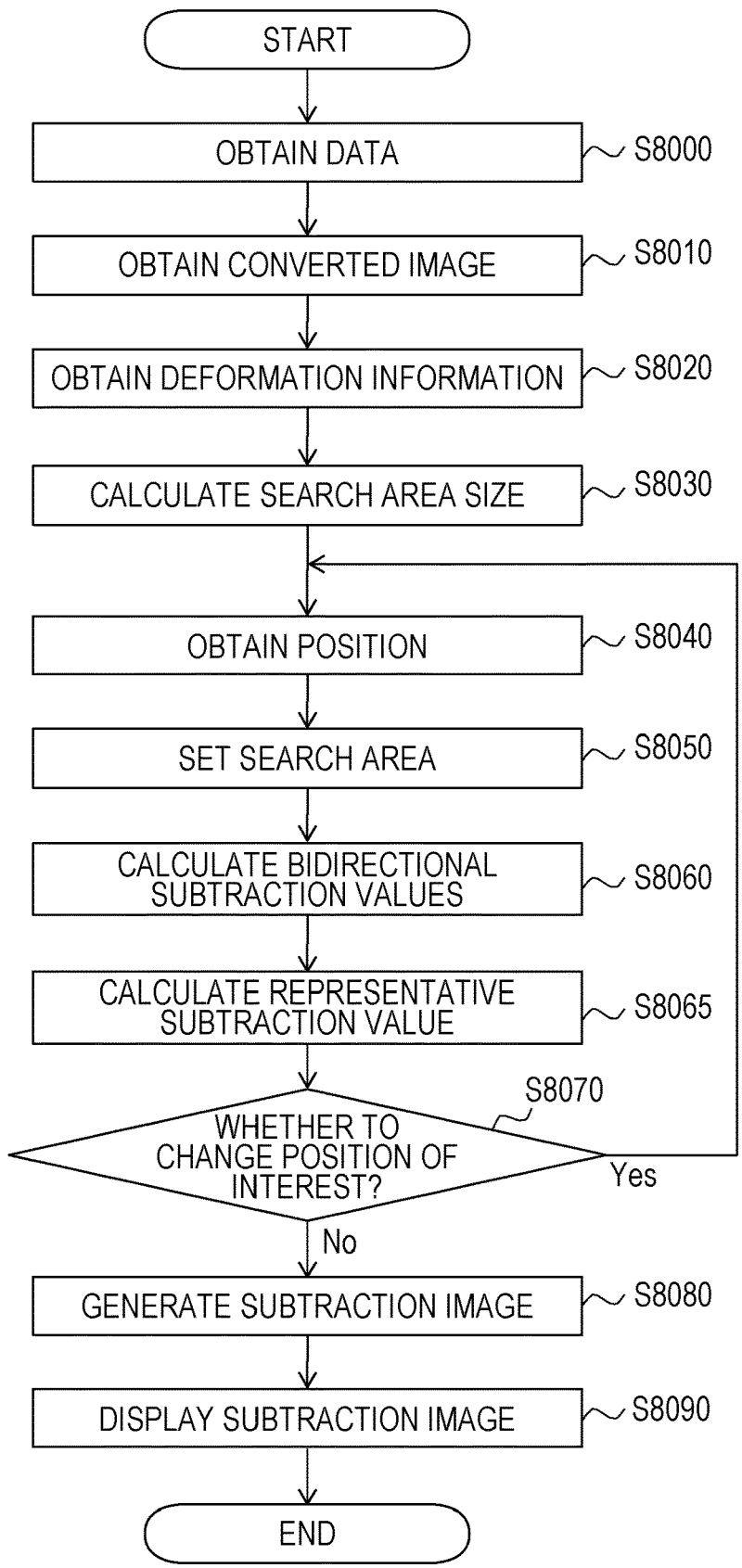
FIG. 8 is a flow chart illustrating an example of the overall processing procedure according to a fourth embodiment.

FIG. 8 illustrates a flow chart of the overall processing procedure performed by the image processing apparatus 100. In steps S8000 to S8040 and S8070 to S8090, since the processes respectively similar to steps S2000 to S2040 and S2070 to S2090 according to the first embodiment are performed, the descriptions thereof will be omitted. Hereinafter, only a different part from the flow chart in FIG. 2 will be described.

(S8050) (Setting of Search Area)

In step S8050, the search area setting unit 1060 sets a first search area made up of the search area size calculated in step S8030 in the surrounding while the position of interest on the first converted image is set as the center. In addition, similarly as in step S2050 according to the first embodiment, a second search area made up of the search area size calculated in step S8030 is set in the surrounding while the correspondence position on the second converted image is set as the center. Then, information of the set first search area and second search area is output to the subtraction calculation unit 1070.

(S8060) (Calculation of Bidirectional Subtraction Values)

In step S8060, the subtraction calculation unit 1070 calculates the subtraction value (in the forward direction) in the position of interest on the basis of the density value of the position of interest on the first converted image and the density value of each of the pixels in the second search area on the second converted image similarly as in step S2060 according to the first embodiment. Furthermore, the subtraction calculation unit 1070 calculates the subtraction value (in the backward direction) in the position of interest on the basis of the density value of the correspondence position on the second converted image and the density value of each of the pixels in the first search area on the first converted image. This processing can be performed similarly as in step S2060 according to the first embodiment since only the position of interest and the correspondence position are swapped. It should be noted that various methods described in step S2060 can be used for the calculation of the subtraction value.

(S8065) (Calculation of Representative Subtraction Value)

In step S8065, the subtraction calculation unit 1070 integrates the subtraction value in the forward direction and the subtraction value in the backward direction which are calculated in step S8060 to each other to calculate the representative subtraction value. For example, absolute values of both are compared with each other, and the subtraction value having the higher absolute value is obtained as the representative subtraction value. Then, the obtained representative subtraction value is output to the subtraction image generation unit 1080 as the density value in the position of interest of the subtraction image.

In a signal of a lesion having a small size which only exists in one of the images among the first image and the second image, the subtraction value is captured in one of the forward direction and the backward direction, and the subtraction value cannot be captured in the other direction in some cases. The signal may disappear in the subtraction value on one direction in some cases, but when the representative subtraction value is calculated by using the bidirectional subtraction values, the above-described subtraction value can be kept on the subtraction image.

According to the present embodiment, the subtraction value having the higher absolute value is set as the representative subtraction value, but the subtraction value having the lower absolute value may be set as the representative subtraction value. In addition, an average value of the subtraction value in the forward direction and the subtraction value in the backward direction may be set as the representative subtraction value. According to this, while the subtraction value with the signal that exists in only one of the images is decreased, the signal of the noise can be further suppressed.

It should be noted that, according to the present embodiment, the size of the search area does not necessarily need to be adaptively decided on the basis of the pixel size of the input image. That is, the preferable search area size with respect to the typical pixel size may be previously set as a default to be used. In this case, the search area size calculation unit 1040 and the processing in step S8030 become unnecessary.

According to the present embodiment, an advantage is attained that a risk of deleting the signal of the lesion having the small size which only exists in one of the images can be abbreviated as compared with the first embodiment.

Fifth Embodiment

The image processing apparatus according to the present embodiment is an apparatus that generates a three-dimensional subtraction image between the plurality of three-dimensional image (the first image and the second image) similarly as in the first embodiment. According to the present embodiment, an example will be described in which the present invention is implemented by a still simpler configuration. Hereinafter, a configuration and the processing according to the present embodiment will be described by using FIG. 9 and FIG. 10.

Figure 9:
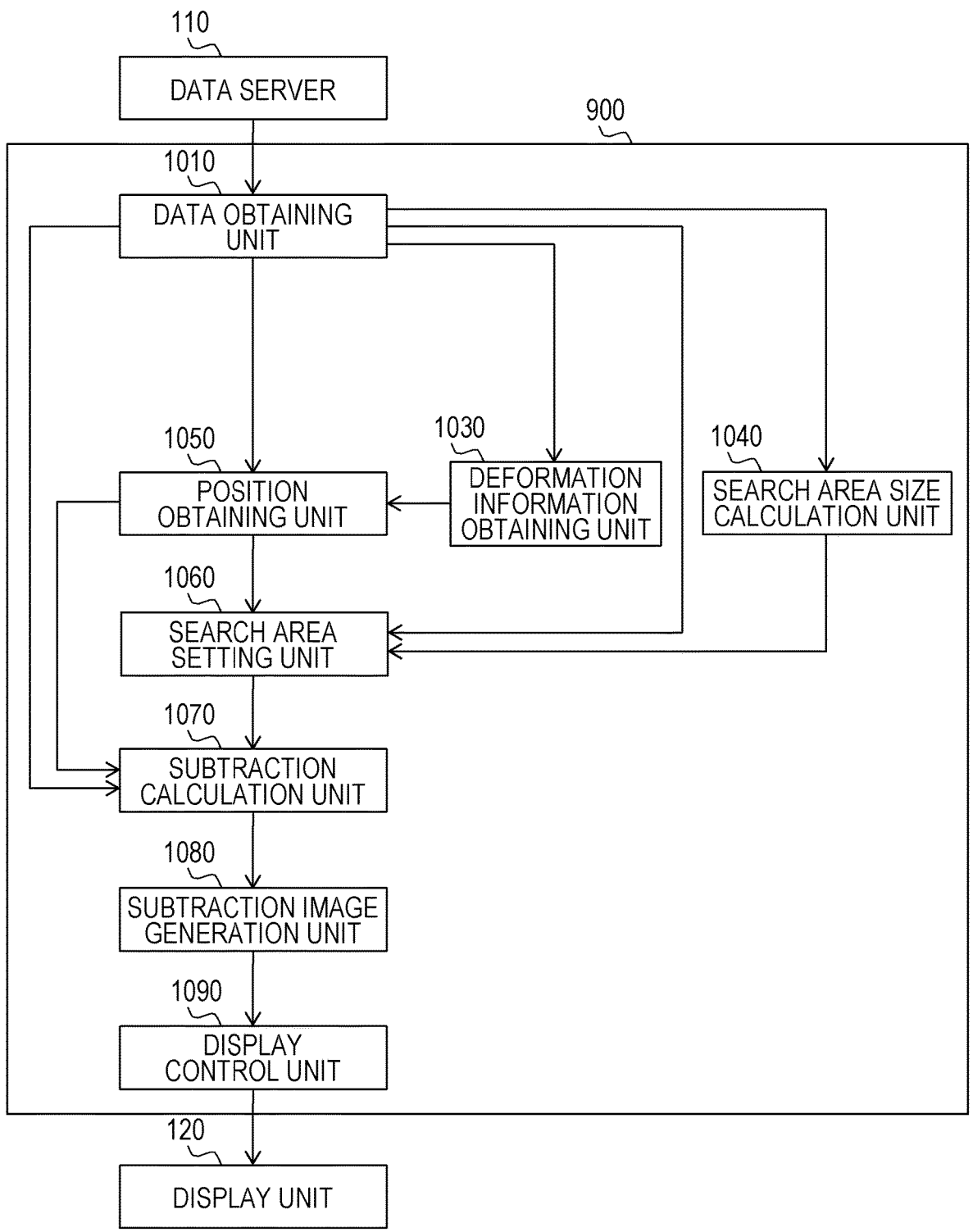
FIG. 9 illustrates an example of the device configuration of the image processing apparatus according to a fifth embodiment.

FIG. 9 illustrates a configuration of the image diagnosis system according to the present embodiment. Since the data server 110 and the display unit 120 have the same functions as the first embodiment, the descriptions thereof will be omitted.

An image processing apparatus 900 is constituted by the following components. Since the data obtaining unit 1010, the search area size calculation unit 1040, the subtraction image generation unit 1080, and the display control unit 1090 have the same functions as the first embodiment, the descriptions thereof will be omitted. With regard to the other configurations, functions thereof will be described below.

The deformation information obtaining unit 1030 obtains the deformation information representing the correspondence relationship of the positions on the images between the first image and the second image. The position obtaining unit 1050 obtains the position of interest on the first image and obtains the correspondence position on the second image corresponding to the position of interest on the first image by using the deformation information obtained by the deformation information obtaining unit 1030. The search area setting unit 1060 sets the search area made up of the search area size in the surrounding of the correspondence position on the second image. The subtraction calculation unit 1070 calculates the subtraction value in the position of interest on the basis of the density value of the pixel of interest on the first image and the density values of the plurality of pixels in the search area on the second image.

Figure 10:
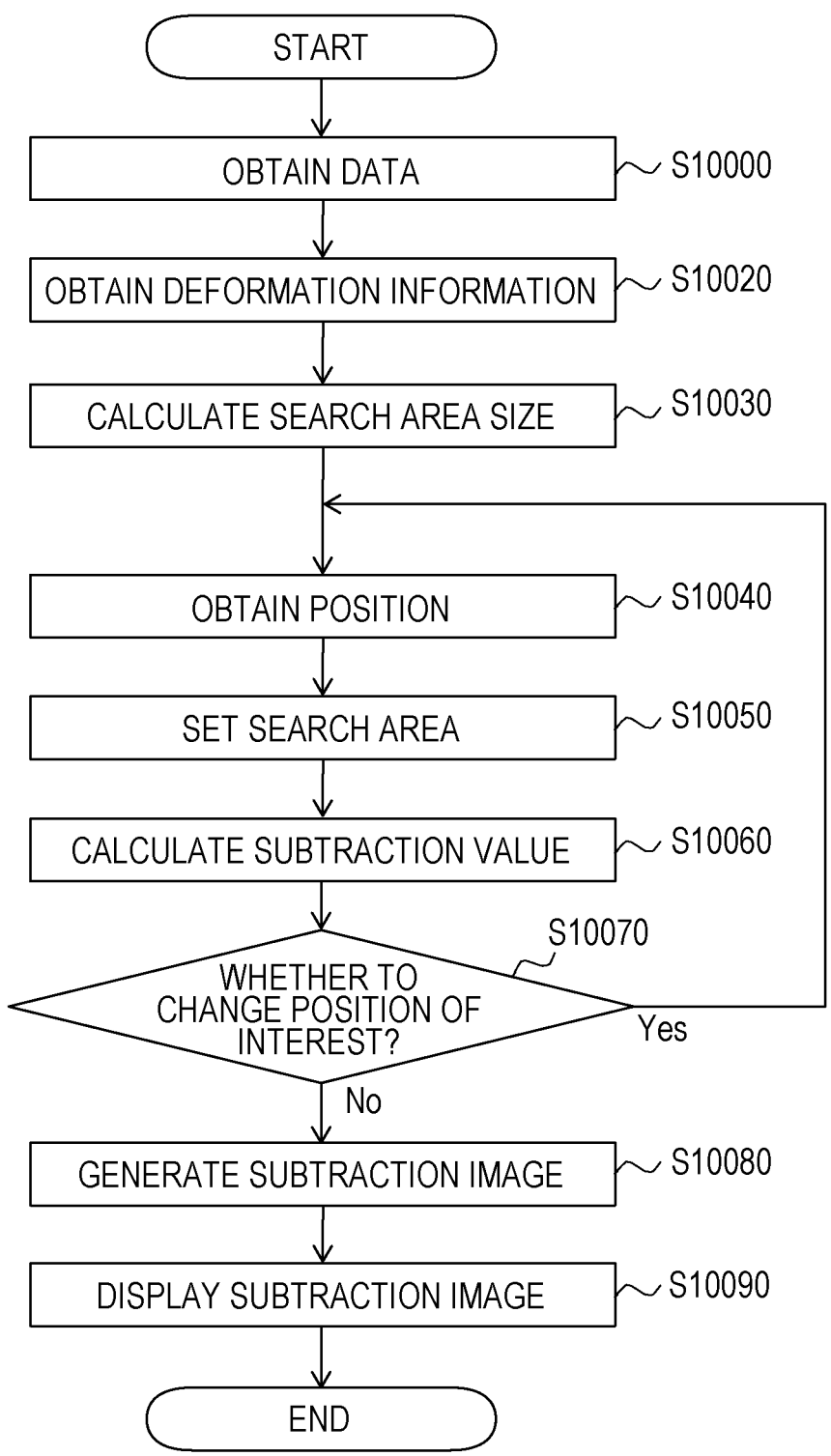
FIG. 10 is a flow chart illustrating an example of the overall processing procedure according to the fifth embodiment.

FIG. 10 illustrates a flow chart of the overall processing procedure performed by the image processing apparatus 900. In step S10090, since the processing similar to step S2090 according to the first embodiment is performed, the descriptions thereof will be omitted. Hereinafter, only a different part from the flow chart in FIG. 2 will be described.

(S10000) (Obtainment of Data)

In step S10000, the data obtaining unit 1010 obtains the first image and the second image input to the image processing apparatus 900. Then, the obtained first image and second image are output to the deformation information obtaining unit 1030, the position obtaining unit 1050, the search area setting unit 1060, and the subtraction calculation unit 1070. In addition, the information related to the pixel sizes of the first image and the second image is output to the search area size calculation unit 1040.

(S10020) (Obtainment of Deformation Information)

In step S10020, the deformation information obtaining unit 1030 obtains the deformation information such that the pixels representing the same site are substantially matched with each other between the first image and the second image. That is, the registration processing between (deformation estimating processing) between the first image and the second image is performed. Then, the obtained deformation information is output to the position obtaining unit 1050.

According to the present embodiment, the deformation information can be obtained by the related-art image processing technique similarly as in the first embodiment.

(S10030) (Calculation of Search Area Size)

In step S10030, the search area size calculation unit 1040 calculates the search area size used for the calculation of the subtraction value on the basis of the pixel size of the first image and the pixel size of the second image. Then, the calculated search area size is output to the search area setting unit 1060.

According to the present embodiment, similarly as in the first embodiment, the nature that the positions of the pixels where the original imaging signal of the subject is most reflected are displaced by the sum of half of the pixel size of each of the original images at maximum by the displacement of the discretized positions at the time of the image generation between the first image and the second image is used. That is, the sum of half of the pixel size of each of the first image and the second image is calculated as the search area size.

(S10040) (Obtainment of Position)

In step S10040, the position obtaining unit 1050 obtains the position of interest on the first image (pixel of interest) and obtains the correspondence position on the second image corresponding to the position of interest by using the deformation information obtained in step S10020. Then, the obtained positions are output to the search area setting unit 1060 and the subtraction calculation unit 1070.

(S10050) (Setting of Search Area)

In step S10050, the search area setting unit 1060 sets the search area made up of the search area size calculated in step S10030 in the surrounding while the correspondence position on the second image is set as the center. Then, the information of the set search area is output to the subtraction calculation unit 1070.

(S10060) (Calculation of Subtraction Value)

In step S10060, the subtraction calculation unit 1070 obtains the subtraction value assigned to the subtraction image on the basis of the density values of the positions of interest on the first image and the density value in each of the plurality of positions in the search area on the second image which are obtained in step S10040. Then, the subtraction value is output to the subtraction image generation unit 1080.

According to the first embodiment, the subtraction value is calculated from the density values of the reference image (the first image or the first converted image) and the second converted image, but, according to the present embodiment, the subtraction value is calculated from the density values of the first image and the second image similarly as in step S2060 according to the first embodiment. That is, a subtraction between the density value of the positions of interest on the first image and the density value of each of the plurality of positions in the search area on the second image is calculated, and the minimum value among those is obtained as the subtraction value assigned to the subtraction image. It should be noted that, when the density value is obtained from the plurality of positions in the search area on the second image, the density value may be obtained from each of the pixels while the positions of all the pixels in the search area are set as the plurality of positions. Alternatively, as the plurality of positions in the search area, measurement points at a predetermined interval smaller than a pixel pitch may be set in the search area to obtain the density value in each of the measurement points from the density value the neighboring pixel by performing an interpolation.

(S10070) (Whether to Change Position of Interest?)

In step S10070, the position obtaining unit 1050 determines whether or not the subtraction values in all the positions (all the pixels) on the first image are calculated. In a case where the subtraction values in all the positions are calculated, the processing proceeds to step S10080. On the other hand, in a case where the subtraction values in all the positions are not obtained, the processing returns to step S10040.

It should be noted that, according to the present embodiment, the calculation of the subtraction value may be performed in part of the positions on the first image which are previously extracted by the related-art image processing technology instead of all the positions on the first image. According to this, it is possible to reduce the processing time necessary for the noise reduction.

(S10080) (Generation of Subtraction Image)

In step S10080, the subtraction image generation unit 1080 generates the subtraction image (first subtraction image) in which the subtraction value in each of the positions (pixels) on the first image is set as the density value. Then, the obtained subtraction image is saved in the data server 110. In addition, the obtained subtraction image is output to the display control unit 1090. It should be noted that the general subtraction image (second subtraction image) in which the second subtraction value (subtraction between the density value of the position of interest on the first image and the density value of the correspondence position on the second image) which is calculated in step S10060 is set as the density value may also be generated as well.

In the above-described manner, the processing of the image processing apparatus 900 is implemented.

As described above, an advantage similar to the first embodiment can be attained without obtaining the first converted image and the second converted image. That is, when the subtraction value is calculated from the search area having the necessary minimum size in which the displacement of the discretized positions is taken into account, the user can examine the subtraction image in which the necessary signal on the subtraction image is kept and also the noise generated from the subtraction in the density values due to the displacement of the discretized positions between the images is reduced. It should be noted that, with regard to each of the second to fifth embodiments too, the implementation can be performed without obtaining the first converted image and the second converted image similarly as in the present embodiment.

Sixth Embodiment

The image processing apparatus according to the present embodiment is an apparatus that generates a three-dimensional subtraction image between the first image and the second image similarly as in the first embodiment. It should be noted however that it is a feature that, in a case where the pixel sizes between the images are different from each other, the image processing apparatus according to the present embodiment generates the subtraction image having the reduced noise which is derived from the subtraction in the density values between the images which is generated when the pixel sizes are different from each other. Hereinafter, the image processing apparatus according to the present embodiment will be described.

Normally, when the continuous signal data obtained from the subject like the CT image is converted into the density value of the discretized pixel to reconstruct the image, a signal data weighted average value in a predetermined section (for example, an in-plane pixel size or a slice thickness of a slice image) is used. That is, the density value of the pixel having the large pixel size is calculated while the signal data in a wider range is smoothed as compared with the small pixel. In a case where the pixel size of the second image is smaller than that of the first image, the image processing apparatus according to the present embodiment approximately regards the density value of the second image as the signal data. Then, when the density value of the pixel in the area on the second image having the same size as the single pixel of the first image is smoothed, the density value generated from the signal data of the area having the same size as the single pixel of the first image is approximately obtained, and a second smoothed image in which the second image is smoothed is generated. Then, the processing for generating the subtraction image which is similar to the first embodiment is performed by using the generated second smoothed image instead of the second image. According to this, since the smoothing area on the second image where the subtraction in the density value with the pixel of interest on the first image becomes the lowest is selected, and the change in the density value caused by a minute displacement of the area to be smoothed can be absorbed. On the other hand, in a case where the pixel size of the first image is smaller than that of the second image, similarly, the processing for generating the subtraction image which is similar to the first embodiment is performed by using a first smoothed image obtained by smoothing the first image instead of the first image. According to this, in a case where the two images having the different pixel sizes are set as the inputs, the user can observe the subtraction image having the reduced noise as compared with the first embodiment.

Hereinafter, a configuration and processing according to the present embodiment will be described by using FIG. 11 and FIG. 12.

Figure 11:
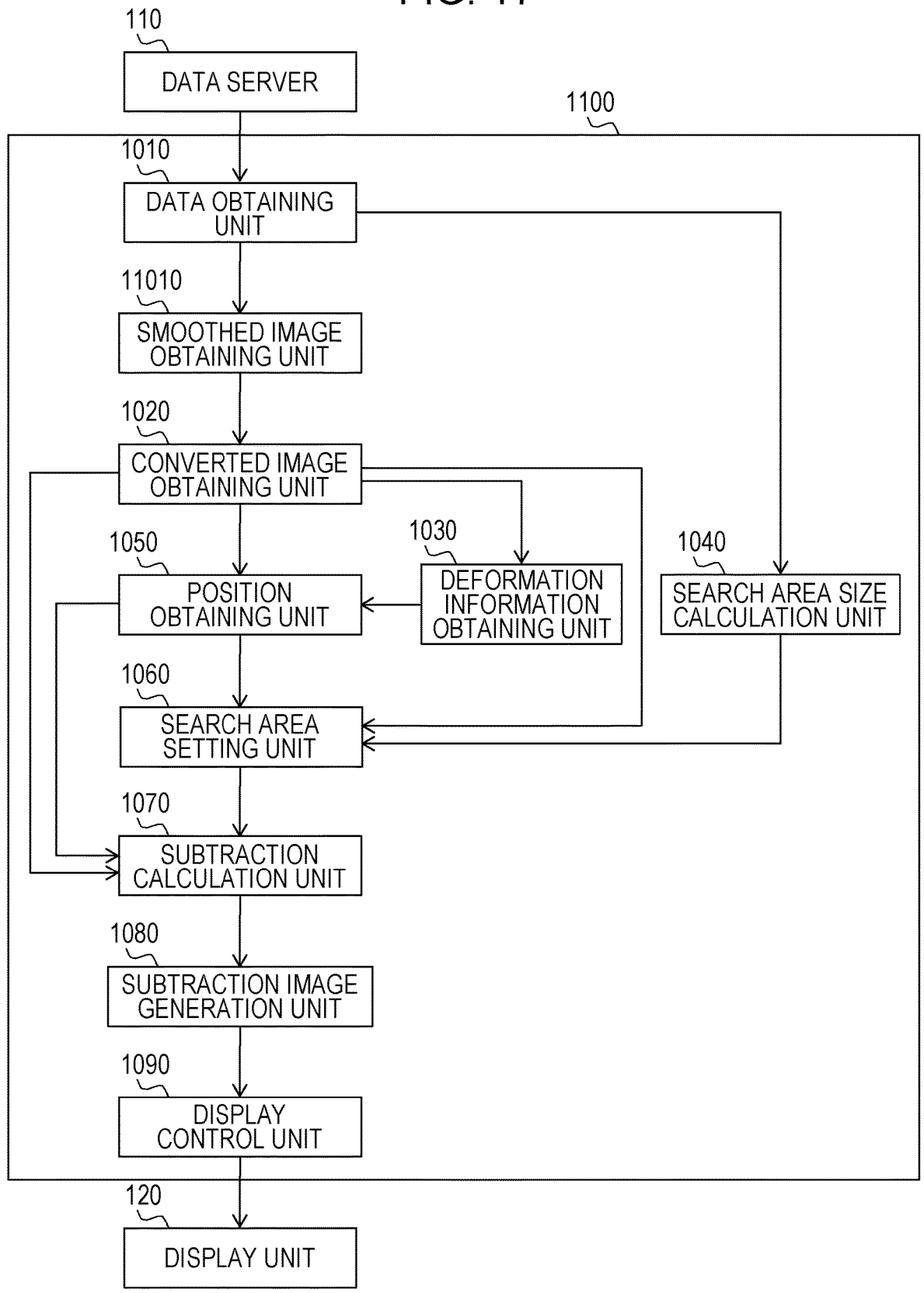
FIG. 11 illustrates an example of the device configuration of the image processing apparatus according to a sixth embodiment.

FIG. 11 illustrates a configuration of the image diagnosis system according to the present embodiment. With regard to a smoothed image obtaining unit 11010, a function thereof will be described below. Since the other configurations have the same functions as the first embodiment, the descriptions thereof will be omitted.

In a case where the pixel size of the second image is smaller than that of the first image, the smoothed image obtaining unit 11010 obtains the second smoothed image in which the second image is smoothed. On the other hand, in a case where the pixel size of the first image is smaller than that of the second image, the smoothed image obtaining unit 11010 obtains the first smoothed image in which the first image is smoothed.

Figure 12:
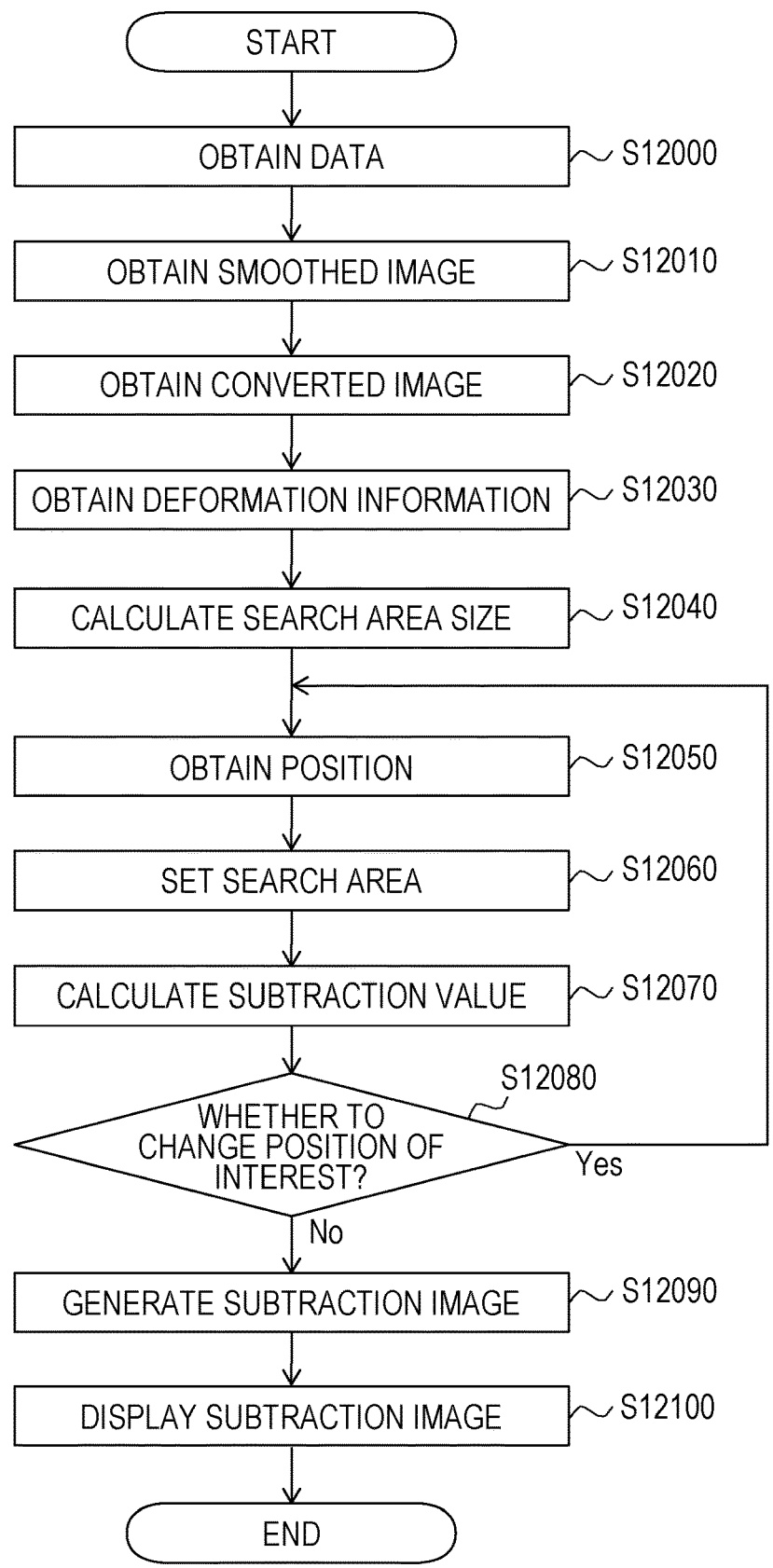
FIG. 12 is a flow chart illustrating an example of the overall processing procedure according to the sixth embodiment.

FIG. 12 illustrates a flow chart of the overall processing procedure performed by an image processing apparatus 1100. In steps S12030 to S12100, since the processes in steps S2020 to S2090 according to the first embodiment are respectively performed, the descriptions thereof will be omitted. Hereinafter, only a different part from the flow chart in FIG. 2 will be described.

(S12000) (Obtainment of Data)

In step S10000, the data obtaining unit 1010 obtains the first image and the second image to be input to the image processing apparatus 1100. Then, the obtained first image and second image are output to a smoothed image obtaining unit 1910. In addition, the information related to the pixel sizes of the first image and the second image is output to the search area size calculation unit 1040.

(S12010) (Obtainment of Smoothed Image)

In step S12010, in a case where the pixel size of the second image is smaller than that of the first image, the smoothed image obtaining unit 1910 obtains the second smoothed image in which the second image is smoothed. Then, the obtained second smoothed image and first image are output to the converted image obtaining unit 1020. In this case, the image processing apparatus 1100 performs the subsequent processing by replacing the second image with the second smoothed image. On the other hand, in a case where the pixel size of the first image is smaller than the second image, the first smoothed image in which the first image is smoothed is obtained. Then, the obtained first smoothed image and second image are output to the converted image obtaining unit 1020. In this case, the image processing apparatus 1100 performs the subsequent processing by replacing the first image with the first smoothed image.

According to the present embodiment, to apply processing, in which the processing for reconstructing the image having the larger pixel size (hereinafter, a large pixel image) from the signal data is approximated, to the image having the smaller pixel size (hereinafter, a small pixel image), the smoothed image obtaining unit 1910 smoothes the small pixel image by using a kernel having the same size as the pixel size of the large pixel image. For example, a case is supposed where the respective pixel sizes in the x, y, and z-axis directions of the large pixel image are 1.5 mm, 1.5 mm, and 5 mm, and the respective pixel sizes of the small pixel image are 0.5 mm, 0.5 mm, and 1 mm. At this time, the kernel sizes corresponds to 1.5 mm×1.5 mm×5 mm, and this is the size corresponding to 3×3×5 pixels on the small pixel image. Related-art smoothing processing is performed by using this kernel. As the smoothing processing, processing for evenly averaging the density values for 3×3×5 pixels may be performed, or processing for calculating a weighted average as in the smoothing processing by a Gaussian filter may also be performed. It should be noted that, since the in-slice resolution (=the pixel sizes in the x and y directions) in the general CT image is a sufficiently high resolution in many cases, a configuration may be adopted in which the noise reduction is not performed with regard to the x and y directions. In this case, the kernel sizes in the x and y-axis directions may be set as 1 pixel, and only the density value in the z-axis direction may be smoothed.

In the above-described example, a ratio of the pixel sizes between the images is an odd-numbered multiple. That is, the kernel sizes in the respective axis directions on the small pixel image are set as the odd-numbered pixels. Hereinafter, an example in which the ratio of the pixel sizes between the images is an even-numbered multiple will be described. For example, in a case where the respective pixel sizes in the x, y, and z-axis directions of the large pixel image are 0.5 mm, 0.5 mm, 4 mm, and the respective pixel sizes of the small pixel image are 0.5 mm, 0.5 mm, and 1 mm, the kernel size corresponds to 1×1×4 pixels on the small pixel image. In general, in a case where filter processing is performed by using the kernel, the processing is performed while the kernel sizes in the axis directions are set as the odd-numbered pixels, and the pixel of the filter processing target and the pixels in the positive and negative directions of the axis while the pixel is set as the center are used evenly (2 pixels each in the case of 5 pixels). However, in a case where the kernel size is even-numbered pixels like 4 pixels, the pixels in the positive and negative directions of the axis cannot be evenly used. For this reason, the image in which the resolution of the small pixel image is converted is generated such that the pixel size of the large pixel image becomes the odd-numbered multiple with respect to the small pixel image. More specifically, the pixel size of the small pixel image is converted such that the pixel size of the large pixel image becomes the odd-numbered multiple with respect to the image in which the resolution of the small pixel image is converted and to also have the closest value lower than or equal to the pixel size of the original small pixel image. In the above-described example, since the pixel size in only the z-axis direction is the even-numbered multiple, the resolution in only the z direction is converted. That is, when the pixel sizes of the small pixel image are converted into 0.5 mm, 0.5 mm, and 0.8 mm, the kernel size on the image in which the resolution is converted corresponds to 1×1×5 pixels, and it is possible to smooth the density value by using evenly the pixels in the positive and negative directions of the axis.

According to the present embodiment, the density value of the small pixel image is approximately regarded as the signal data, and the density value of the smoothed image is calculated from the approximated signal data. A method of calculating the density value from the signal data is preferably similar to the method of actually generating the density value of the large pixel image from the signal data to reconstruct the image. That is, in a case where a reconstruction algorithm for the large pixel image is already established, the density value of the smoothed image may be calculated in accordance with the algorithm.

It should be noted that, when a value obtained by smoothing the density values the pixels in the range indicated by the kernel is calculated, all the pixels in the range may be used, or smoothing of the density values of the pixels sampled at an arbitrary interval may be performed. When the pixels are sampled, the smoothing processing can be accelerated.

It should be noted that, according to the present embodiment, in a case where the pixel sizes of the first image and the second image are equal to each or a case where the subtraction in the pixel sizes is lower than or equal to the threshold, the first image and the second image are output to the converted image obtaining unit 1020, and the present step may be omitted. In this case, the processing similar to the first embodiment is implemented.

(S12020) (Obtainment of Converted Image)

In step S12020, similarly as in the first embodiment, the converted image obtaining unit 1020 obtains the first converted image in which the resolution of the first image (or the first smoothed image) is converted and the second converted image in which the resolution of the second image (or the second smoothed image) is converted such that the pixel sizes between the two images becomes the same. Then, the generated converted images are output to the deformation information obtaining unit 1030, the position obtaining unit 1050, the search area setting unit 1060, and the subtraction calculation unit 1070.

In the above-described manner, the processing of the image processing apparatus 1100 is implemented.

According to the present embodiment, when the smoothing processing is performed such that the image having the smaller pixel size is approximated to the image having the larger pixel size between the images having the different pixel sizes and also the subtraction calculation is performed, the user can observe the subtraction image in which the noise generated from the subtraction in the pixel sizes as compared with the first embodiment.

It should be noted that, according to the above-described embodiment, the smoothing processing is applied to the second image in a case where the pixel size of the second image is smaller than that of the first image, but a similar benefit can be attained even when the smoothing processing is applied to the second converted image. Similarly, in a case where the pixel size of the first image is smaller than that of the second image, the smoothing processing may be applied to the first converted image instead of the first image. At this time, the kernel size for the smoothing may be decided on the basis of the pixel size of the original image instead of the pixel size of the converted image.

It should be noted that the processing similar to the present embodiment also can be performed in the second embodiment to the fifth embodiment. That is, after the obtainment of the image data, the smoothed image is generated in which the image having the smaller pixel size among the first image and the second image is smoothed in accordance with the image having the larger pixel size, and the similar noise reduction effect can be attained by performing the subsequent processing by replacing the original image with the smoothed image. Herein, according to the third embodiment, in a case where the pixel size of the second image is smaller than that of the first image, the smoothed image in which the smoothing processing is applied to the second deformed converted image may be generated and used by replacing the second deformed converted image. In addition, according to the respective embodiments, the first image and the second image (or the converted images) to which the smoothing is not applied may be used for the deformation information obtaining processing implemented by the deformation information obtaining unit, and the smoothed image (or the converted image) may be used for only the subtraction value calculation processing performed by the subtraction calculation unit.

(Modified Example 6-1) (Obtainment of Deformation Information from Outside)

According to the present embodiment, the deformation information is obtained by using the image after the smoothing processing, but as a configuration for obtaining the deformation information from the data server 110, the processing for obtaining the deformation information may be skipped. Then, the subtraction image between the first image or the first converted image and the second smoothed image may be generated by using the deformation information. For example, in a case where the user who observes the subtraction image generated by the image processing apparatus according to the first embodiment determines that the noise generated by the subtraction in the pixel sizes needs to be reduced, the image processing apparatus according to the present embodiment can generate the subtraction image in which the noise is reduced by using the already obtained deformation information. According to this, since the processing for obtaining the deformation information can be skipped, the processing can be accelerated.

(Modified Example 6-2) (Smoothing Method that is not Pixel Separation)

According to the present embodiment, the image in which the resolution of the second image is converted is smoothed such that the pixel size of the first image becomes the odd-numbered multiple with respect to the second image, but the resolution does not necessarily need to be converted. For example, while the pixel as the smoothing target on the second image is set as the center, a first area having the same pixel size of the first image is set, and the smoothing processing may be performed in accordance with the density values of the pixels included in the first area and a volume ratio of the pixels. More specifically, in a case where the pixels of the second image are completely included in the first area, a weighting coefficient related to the density values of the pixels is set as 1. On the other hand, when only half of the pixels are included in the first area, a weighting coefficient related to the density values of the pixels is set as 0.5. Then, it is possible to obtain the second smoothed image in which a weighted average value of the density values of all the pixels included in the first area is set as the density value. According to this, an equivalent benefit can be attained even when the resolution of the second image is not converted such as that the pixel size of the first image becomes the odd-numbered multiple with respect to the second image.

Other Embodiments

The exemplary embodiments have been described in detail above, but the present invention can adopt an embodiment as a system, an apparatus, a method, a program, or a recording medium (storage medium), for example. Specifically, the present invention may be applied to a system constituted by a plurality of devices (such as, for example, a host computer, an interface device, an imaging apparatus, and a Web application) and may also be applied to an apparatus constituted by a single device.

In addition, the aim of the present invention is of course achieved by the following configuration. That is, a recording medium (storage medium) that records a program code (computer program) of software that realizes the functions of the above-described embodiments is supplied to a system or an apparatus. The above-described storage medium is of course a computer-readable storage medium. Then, a computer (or a CPU or an MPU) of the system or the apparatus reads out the program code stored in the recording medium to be executed. In this case, the program code itself read out from the recording medium realizes the functions of the above-described embodiments, and the recording medium that records the program code constitutes the present invention. It should be noted that the respective functions included in the image processing apparatus according to the above-described embodiment are realized when at least one processor included in the image processing apparatus executes the program stored in at least one memory. There is no restriction on types of processors, and processors of plural types may also be used.

In addition, arbitrary embodiments from among the above-described plurality of embodiments may also be combined.

According to the disclosure of the present specification, a necessary signal is kept on a subtraction image, and also, it becomes possible to reduce noise.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing a program; and
one or more processors which, by executing the program, function as a plurality of means comprising:
image obtaining means for obtaining a first image and a second image in which a subject is captured;
search area size calculation means for calculating a search area size on a basis of a pixel size of the first image and a pixel size of the second image;
position obtaining means for obtaining a position of interest on the first image and a correspondence position on the second image corresponding to the position of interest;
search area setting means for setting a search area made up of the search area size in a surrounding of the correspondence position on the second image; and
subtraction means for deciding a subtraction value corresponding to the position of interest on a basis of a density value of the position of interest on the first image and density values of a plurality of positions in the search area on the second image.

2. The image processing apparatus according to claim 1, wherein the search area size calculation means calculates the search area size on a basis of a sum of pixel sizes in respective axis directions of the first image and the second image.

3. The image processing apparatus according to claim 1, further comprising:
deformation information obtaining means for obtaining deformation information between the first image and the second image,
wherein the position obtaining means obtains the correspondence position corresponding to the position of interest on a basis of the deformation information, and
wherein the search area size calculation means obtains a constant to be multiplied with the search area size on a basis of an obtaining method for the deformation information.

4. The image processing apparatus according to claim 1, wherein the subtraction means decides a subtraction value corresponding to the position of interest on a basis of a subtraction value between the density value of the position of interest on the first image and each of the density values of the plurality of positions in the search area on the second image.

5. The image processing apparatus according to claim 1, wherein the subtraction means decides a subtraction value corresponding to the position of interest on a basis of the density value of the position of interest on the first image and a value calculated from the density values of the plurality of positions in the search area on the second image.

6. The image processing apparatus according to claim 1, further comprising:
smoothing means for generating a smoothed image in which smoothing processing is applied to an image having a smaller pixel size among the first image and the second image,
wherein the subtraction means decides the subtraction value by replacing the first image or the second image corresponding to an original image of the smoothed image with the smoothed image.

7. The image processing apparatus according to claim 6, wherein the smoothing means decides a parameter of the smoothing processing on a basis of a pixel size of at least one of the first image and the second image.

8. The image processing apparatus according to claim 1, wherein the first image is converted into a first converted image having a different pixel size from a pixel size of the first image, and the second image is converted into a second converted image having a different pixel size from a pixel size of the second image.

9. The image processing apparatus according to claim 1, further comprising:
deforming information obtaining means for obtaining deformation information between the first image and the second image;
projection means for obtaining a deformed search area by projecting, on a basis of the deformation information, the search area onto a deformed image obtained by deforming the second image on a basis of the deformation information; and
the subtraction means for deciding a subtraction value corresponding to the position of interest on a basis of a density value of the position of interest on the first image and density values of a plurality of positions in the deformed search area on the deformed image.

10. The image processing apparatus according to claim 1, wherein the subtraction means for deciding a subtraction value corresponding to the position of interest on a basis of a density value of a first position on the first image and distribution information of density values in the search area on the second image.

11. The image processing apparatus according to claim 10, wherein the distribution information of the density values is a density range of the density values in the search area on the second image.

12. The image processing apparatus according to claim 1, wherein
the search area setting means sets a first search area in a surrounding of the position of interest on the first image and sets a second search area in the surrounding of the correspondence position on the second image; and
the subtraction means decides the subtraction value corresponding to the position of interest on a basis of a first subtraction value based on the density value of the position of interest on the first image and density values of a plurality of positions in the second search area on the second image and a second subtraction value based on a density value of the correspondence position on the second image and density values of a plurality of positions in the first search area on the first image.

13. An image processing apparatus comprising:

image obtaining means for obtaining a first image and a second image in which a subject is captured;

search area size calculation means for calculating a search area size on a basis of a pixel size of the first image and a pixel size of the second image;

conversion means for obtaining a second converted image in which a resolution is converted such that the second image has a different pixel size;

deformation information obtaining means for obtaining deformation information between a reference image and the second converted image when the first image or a first converted image in which a resolution is converted such that the first image has a different pixel size is set as the reference image;

position obtaining means for a position of interest on the reference image and a correspondence position on the second converted image corresponding to the position of interest on a basis of the deformation information;

search area setting means for setting a search area made up of the search area size in a surrounding of the correspondence position on the second converted image; and subtraction means for deciding a subtraction value corresponding to the position of interest on a basis of a density value of the position of interest on the reference image and density values of a plurality of positions in the search area on the second converted image.

14. An image processing apparatus comprising:

image obtaining means for obtaining a first image and a second image in which a subject is captured;

search area size calculation means for calculating a search area size on a basis of a pixel size of the first image and a pixel size of the second image;

deformation information obtaining means for obtaining deformation information between the first image and the second image;

position obtaining means for obtaining a position of interest on the first image and a correspondence position on the second image corresponding to the position of interest on a basis of the deformation information;

search area setting means for setting a search area made up of the search area size in a surrounding of the correspondence position on the second image;

projection means for obtaining a deformed search area by projecting, on a basis of the deformation information, the search area onto a deformed image obtained by deforming the second image on a basis of the deformation information; and subtraction means for deciding a subtraction value corresponding to the position of interest on a basis of a density value of the position of interest on the first image and density values of a plurality of positions in the deformed search area on the deformed image.

15. An image processing method comprising:

an image obtaining step of obtaining a first image and a second image in which a subject is captured;

a search area size calculation step of calculating a search area size on a basis of a pixel size of the first image and a pixel size of the second image;

a position obtaining step of obtaining a position of interest on the first image and a correspondence position on the second image corresponding to the position of interest;

a search area setting step of setting a search area made up of the search area size in a surrounding of the correspondence position on the second image; and a subtraction step of deciding a subtraction value corresponding to the position of interest on a basis of a density value of the position of interest on the first image and density values of a plurality of positions in the search area on the second image.

16. A non-transitory computer-readable storage medium storing a program for causing a computer to execute the image processing method according to claim 15.

* * * * *